(12) United States Patent
Schaeffer

(10) Patent No.: US 10,814,098 B2
(45) Date of Patent: Oct. 27, 2020

(54) DEFLECTABLE CATHETERS, SYSTEMS, AND METHODS FOR THE VISUALIZATION AND TREATMENT OF BODILY PASSAGES

(71) Applicant: Cook Medical Technologies LLC, Bloomington, IN (US)

(72) Inventor: Darin Schaeffer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 326 days.

(21) Appl. No.: 15/947,947

(22) Filed: Apr. 9, 2018

(65) Prior Publication Data

US 2018/0221625 A1 Aug. 9, 2018

Related U.S. Application Data

(63) Continuation of application No. 14/633,561, filed on Feb. 27, 2015, now Pat. No. 9,937,323.

(60) Provisional application No. 61/946,231, filed on Feb. 28, 2014.

(51) Int. Cl.
| | | |
|---|---|---|
| *A61M 31/00* | (2006.01) | |
| *A61M 37/00* | (2006.01) | |
| *A61M 25/01* | (2006.01) | |
| *A61M 25/00* | (2006.01) | |
| *A61B 1/00* | (2006.01) | |

(Continued)

(52) U.S. Cl.
CPC ..... *A61M 25/0138* (2013.01); *A61B 1/00066* (2013.01); *A61B 1/05* (2013.01); *A61B 1/07* (2013.01); *A61B 1/233* (2013.01); *A61M 25/0023* (2013.01); *A61M 25/0136* (2013.01);

(Continued)

(58) Field of Classification Search
CPC ...... A61M 2025/0161; A61M 25/0023; A61M 25/0136; A61M 25/0138; A61M 25/0147; A61B 1/05; A61B 1/07
See application file for complete search history.

(56) References Cited

U.S. PATENT DOCUMENTS 2,649,092 A 8/1953 Wallace
3,081,767 A 3/1963 Hett
(Continued)

FOREIGN PATENT DOCUMENTS

CA 2403030 3/2003
DE 102015220496 A1 4/2017
(Continued)

OTHER PUBLICATIONS

Non-final Office Action dated Sep. 15, 2009 U.S. Appl. No. 11/800,292.
(Continued)

*Primary Examiner* — Rebecca E Eisenberg
(74) *Attorney, Agent, or Firm* — MacMillan, Sobanski & Todd, LLC

(57) ABSTRACT

Deflectable catheters, systems, and methods of using deflectable catheters are described herein. An embodiment of a deflectable catheter comprises an elongate member, a handle, and a wire member. The elongate member has a shaft and a flexible member. The shaft defines a first lumen and a second lumen and the flexible member defines a passageway. The flexible member is attached to the shaft such that the passageway defined by the flexible member is in communication with each of the first lumen and second lumen defined by the shaft.

19 Claims, 12 Drawing Sheets

(51) Int. Cl.
*A61B 1/05* (2006.01)
*A61B 1/07* (2006.01)
*A61B 1/233* (2006.01)

(52) U.S. Cl.
CPC . *A61M 25/0147* (2013.01); *A61M 2025/0161* (2013.01)

(56) References Cited

U.S. PATENT DOCUMENTS

| | | | |
|---|---|---|---|
| 3,521,620 A | 7/1970 | Cook | |
| 3,625,200 A | 12/1971 | Muller | |
| 4,474,174 A | 10/1984 | Petruzzi | |
| 4,696,544 A | 9/1987 | Costella | |
| 4,719,924 A * | 1/1988 | Crittenden | A61M 25/09033 600/585 |
| 4,726,374 A | 2/1988 | Bales et al. | |
| 4,790,812 A | 12/1988 | Hawkins et al. | |
| 4,826,087 A | 5/1989 | Chinery | |
| 4,841,976 A | 6/1989 | Packard et al. | |
| 4,886,067 A | 12/1989 | Palermo | |
| 5,095,889 A | 3/1992 | Weissmuller et al. | |
| 5,125,395 A | 6/1992 | Adair | |
| 5,176,126 A | 1/1993 | Chikama | |
| 5,308,318 A | 5/1994 | Plassche, Jr. | |
| 5,380,305 A | 1/1995 | Ghouri | |
| 5,441,483 A | 8/1995 | Avitall | |
| 5,447,503 A | 9/1995 | Miller | |
| 5,460,616 A | 10/1995 | Weinstein et al. | |
| 5,470,330 A | 11/1995 | Goldenberg et al. | |
| 5,477,860 A | 12/1995 | Essen-Moller | |
| 5,480,382 A | 1/1996 | Hammerslag et al. | |
| 5,489,278 A | 2/1996 | Abrahamson | |
| 5,509,900 A | 4/1996 | Kirkman | |
| 5,514,128 A | 5/1996 | Hillsman et al. | |
| 5,522,400 A | 6/1996 | Williams | |
| 5,534,007 A | 7/1996 | Germain et al. | |
| 5,642,736 A | 7/1997 | Avitall | |
| 5,643,171 A | 7/1997 | Bradshaw et al. | |
| 5,643,251 A | 7/1997 | Hillsman et al. | |
| 5,658,301 A | 8/1997 | Lamaitre et al. | |
| 5,674,197 A | 10/1997 | van Muiden et al. | |
| 5,685,858 A | 11/1997 | Kawand | |
| 5,718,684 A | 2/1998 | Gupta | |
| 5,738,664 A | 4/1998 | Erskine et al. | |
| 5,769,821 A | 6/1998 | Abrahamson et al. | |
| 5,807,398 A | 9/1998 | Shaknovich | |
| 5,820,546 A | 10/1998 | Ouchi | |
| 5,840,382 A | 11/1998 | Nishide et al. | |
| 5,865,800 A | 2/1999 | Mirarchi et al. | |
| 5,908,403 A | 6/1999 | Bosma et al. | |
| 5,916,214 A | 6/1999 | Cosio et al. | |
| 5,931,811 A | 8/1999 | Haissaguerre et al. | |
| 5,938,582 A | 8/1999 | Ciamacco et al. | |
| 5,954,050 A | 9/1999 | Christopher | |
| 5,989,241 A | 11/1999 | Plishka et al. | |
| 6,027,460 A | 2/2000 | Shturman | |
| 6,033,378 A | 3/2000 | Lundquist et al. | |
| 6,066,125 A | 5/2000 | Webster, Jr. | |
| 6,071,263 A | 6/2000 | Kirkman | |
| 6,096,036 A | 8/2000 | Bowe et al. | |
| 6,117,386 A | 9/2000 | Stiger | |
| 6,123,699 A | 9/2000 | Webster, Jr. | |
| 6,126,649 A | 10/2000 | VanTassel et al. | |
| 6,159,158 A | 12/2000 | Lowe | |
| 6,159,177 A | 12/2000 | Amos, Jr. et al. | |
| 6,183,463 B1 | 2/2001 | Webster, Jr. | |
| 6,206,870 B1 | 3/2001 | Kanner | |
| 6,226,432 B1 | 5/2001 | Gonda et al. | |
| 6,261,284 B1 | 7/2001 | Ouchi | |
| 6,338,735 B1 | 1/2002 | Stevens | |
| 6,383,206 B1 | 5/2002 | Gillick et al. | |
| 6,447,530 B1 | 9/2002 | Ostrovsky et al. | |
| 6,450,988 B1 | 9/2002 | Bradshaw | |
| 6,471,639 B2 | 10/2002 | Rudischhauser et al. | |
| 6,485,500 B1 | 11/2002 | Kokish et al. | |
| 6,491,662 B1 | 12/2002 | Liprie et al. | |
| 6,500,167 B1 | 12/2002 | Webster, Jr. | |
| 6,500,182 B2 | 12/2002 | Foster | |
| 6,508,833 B2 | 1/2003 | Pavcnik et al. | |
| 6,527,737 B2 | 3/2003 | Kaneshige | |
| 6,530,913 B1 | 3/2003 | Giba et al. | |
| 6,533,783 B1 | 3/2003 | Tollner | |
| 6,558,349 B1 | 5/2003 | Kirkman | |
| 6,572,610 B2 | 6/2003 | Kovalcheck et al. | |
| 6,629,987 B1 | 10/2003 | Gambale | |
| 6,673,060 B1 | 1/2004 | Fleming, III | |
| 6,679,860 B2 | 1/2004 | Stiger | |
| 6,692,484 B1 | 2/2004 | Karpiel et al. | |
| 6,695,858 B1 | 2/2004 | Dubrul et al. | |
| 6,755,812 B2 | 6/2004 | Peterson et al. | |
| 6,814,697 B2 | 11/2004 | Ouchi | |
| 6,829,497 B2 | 12/2004 | Mogul | |
| 6,918,929 B2 | 7/2005 | Udipi et al. | |
| 6,932,829 B2 | 8/2005 | Majercak | |
| 7,037,290 B2 | 5/2006 | Gardeski et al. | |
| 7,056,314 B1 | 6/2006 | Florio et al. | |
| 7,144,408 B2 | 12/2006 | Keegan et al. | |
| 7,198,599 B2 | 4/2007 | Goto et al. | |
| 7,232,462 B2 | 6/2007 | Schaeffer | |
| 7,269,453 B2 | 9/2007 | Mogul | |
| 7,273,468 B2 | 9/2007 | Bedell | |
| 7,351,214 B2 | 4/2008 | Burgermeister | |
| 7,361,168 B2 | 4/2008 | Makower et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,503,914 B2 | 3/2009 | Coleman et al. | |
| 7,520,876 B2 | 4/2009 | Ressemann et al. | |
| 7,559,925 B2 | 7/2009 | Goldfarb et al. | |
| 7,641,630 B2 | 1/2010 | Accisano, III et al. | |
| 7,645,272 B2 | 1/2010 | Chang et al. | |
| 7,654,997 B2 | 2/2010 | Makower et al. | |
| 7,658,305 B2 | 2/2010 | Voegele et al. | |
| 7,678,099 B2 | 3/2010 | Ressemann et al. | |
| 7,691,095 B2 | 4/2010 | Bednarek et al. | |
| 7,717,933 B2 | 5/2010 | Becker | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,736,331 B2 | 6/2010 | Accisano, III et al. | |
| 7,740,608 B2 | 6/2010 | Lampropoulos et al. | |
| 7,740,642 B2 | 6/2010 | Becker | |
| 7,753,929 B2 | 7/2010 | Becker | |
| 7,753,930 B2 | 7/2010 | Becker | |
| 7,771,409 B2 | 8/2010 | Chang et al. | |
| 7,785,252 B2 | 8/2010 | Danitz et al. | |
| 7,785,315 B1 | 8/2010 | Muni et al. | |
| 7,803,130 B2 | 9/2010 | Ryan et al. | |
| 7,803,150 B2 | 9/2010 | Chang et al. | |
| 7,811,277 B2 | 10/2010 | Boulais | |
| 7,854,744 B2 | 12/2010 | Becker | |
| 7,867,218 B1 | 1/2011 | Voda | |
| 7,879,061 B2 | 2/2011 | Keith et al. | |
| 7,892,233 B2 | 2/2011 | Hall et al. | |
| 7,909,814 B2 | 3/2011 | Accisano, III et al. | |
| 7,909,862 B2 | 3/2011 | Garrison | |
| 7,918,871 B2 | 4/2011 | Truitt et al. | |
| 7,935,108 B2 | 5/2011 | Baxter et al. | |
| 7,959,601 B2 | 6/2011 | McDaniel et al. | |
| 7,959,644 B2 | 6/2011 | Shriver | |
| 8,029,461 B2 | 10/2011 | Thielen et al. | |
| 8,066,664 B2 | 11/2011 | LaDuca et al. | |
| 8,070,693 B2 | 12/2011 | Ayala et al. | |
| 8,083,879 B2 | 12/2011 | Swinehart et al. | |
| 8,088,101 B2 | 1/2012 | Chang et al. | |
| 8,090,433 B2 | 1/2012 | Makower et al. | |
| 8,100,933 B2 | 1/2012 | Becker | |
| 8,114,062 B2 | 2/2012 | Muni et al. | |
| 8,118,803 B1 | 2/2012 | Chow | |
| 8,123,722 B2 | 2/2012 | Chang et al. | |
| 8,142,422 B2 | 3/2012 | Makower et al. | |
| 8,182,467 B2 | 5/2012 | Nguyen et al. | |
| 8,216,210 B2 | 7/2012 | Ostrovsky et al. | |
| 8,241,266 B2 | 8/2012 | Keith et al. | |

(56) References Cited

U.S. PATENT DOCUMENTS

| | | |
|---|---|---|
| 8,277,478 B2 | 10/2012 | Drontle et al. |
| 8,282,667 B2 | 10/2012 | Drontle et al. |
| 8,317,816 B2 | 11/2012 | Becker |
| 8,369,923 B2 | 2/2013 | de la Rama et al. |
| 8,388,642 B2 | 3/2013 | Muni et al. |
| 8,403,977 B2 | 3/2013 | Case |
| 8,414,473 B2 | 4/2013 | Jenkins et al. |
| 8,425,457 B2 | 4/2013 | John et al. |
| 8,425,466 B2 | 4/2013 | Sargent, Jr. |
| 8,430,864 B2 | 4/2013 | Schultz |
| 8,435,290 B2 | 5/2013 | Clifford et al. |
| 8,496,645 B2 | 7/2013 | Eells et al. |
| 8,535,310 B2 | 9/2013 | Hardin, Jr. et al. |
| 8,535,349 B2 | 9/2013 | Chen et al. |
| 8,579,802 B2 | 11/2013 | Robertson |
| 8,603,185 B2 | 12/2013 | Shah et al. |
| 8,657,805 B2 | 2/2014 | Peh et al. |
| 8,734,426 B2 | 5/2014 | Ahmed et al. |
| 8,740,843 B2 | 6/2014 | Eaton et al. |
| 8,758,231 B2 | 6/2014 | Bunch et al. |
| 9,119,552 B2 | 9/2015 | Baumann et al. |
| 9,314,593 B2 | 4/2016 | Schaeffer |
| 9,375,138 B2 | 6/2016 | Schaeffer et al. |
| 9,895,055 B2 | 2/2018 | Schaeffer et al. |
| 9,937,323 B2 | 4/2018 | Schaeffer |
| 2001/0039450 A1 | 11/2001 | Pavcnik et al. |
| 2002/0115983 A1 | 8/2002 | Sekino et al. |
| 2003/0004460 A1 | 1/2003 | Bedell |
| 2003/0032977 A1 | 2/2003 | Brady |
| 2003/0050694 A1 | 3/2003 | Heneveld et al. |
| 2003/0216711 A1 | 11/2003 | Rabiner et al. |
| 2004/0019252 A1 | 1/2004 | Hirata |
| 2004/0087965 A1 | 5/2004 | Hebert et al. |
| 2004/0087996 A1 | 5/2004 | Forcucci et al. |
| 2004/0225322 A1 | 11/2004 | Garrison et al. |
| 2005/0038412 A1 | 2/2005 | Rabiner et al. |
| 2005/0159728 A1 | 7/2005 | Armour et al. |
| 2005/0171592 A1 | 8/2005 | Majercak |
| 2005/0256452 A1 | 11/2005 | DeMarchi et al. |
| 2006/0063973 A1 | 3/2006 | Makower et al. |
| 2006/0149129 A1 | 7/2006 | Watts et al. |
| 2006/0252993 A1 | 11/2006 | Freed et al. |
| 2007/0093781 A1 | 4/2007 | Kugler et al. |
| 2007/0129751 A1 | 6/2007 | Muni et al. |
| 2007/0167682 A1 | 7/2007 | Goldfarb et al. |
| 2007/0208252 A1 | 9/2007 | Makower |
| 2007/0219464 A1 | 9/2007 | Davis et al. |
| 2007/0250105 A1 | 10/2007 | Ressemann et al. |
| 2007/0282305 A1 | 12/2007 | Goldfarb et al. |
| 2007/0293727 A1 | 12/2007 | Goldfarb et al. |
| 2008/0015472 A1 | 1/2008 | Ressemann et al. |
| 2008/0015544 A1 | 1/2008 | Keith et al. |
| 2008/0039692 A1 | 2/2008 | Hirakawa |
| 2008/0097154 A1 | 4/2008 | Makower et al. |
| 2008/0103521 A1 | 5/2008 | Makower et al. |
| 2008/0119693 A1 | 5/2008 | Makower et al. |
| 2008/0125756 A1 | 5/2008 | Dicarlo et al. |
| 2008/0132938 A1 | 6/2008 | Chang et al. |
| 2008/0172033 A1 | 7/2008 | Keith et al. |
| 2008/0195041 A1 | 8/2008 | Goldfarb et al. |
| 2008/0228085 A1 | 9/2008 | Jenkins et al. |
| 2008/0243067 A1 | 10/2008 | Rottenberg et al. |
| 2008/0249483 A1 | 10/2008 | Slenker et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0287918 A1 | 11/2008 | Rosenman et al. |
| 2008/0319424 A1 | 12/2008 | Muni et al. |
| 2009/0030274 A1 | 1/2009 | Goldfarb et al. |
| 2009/0043299 A1 | 2/2009 | Racz |
| 2009/0044799 A1 | 2/2009 | Qiu |
| 2009/0093823 A1 | 4/2009 | Chang et al. |
| 2009/0187098 A1 | 7/2009 | Makower et al. |
| 2009/0198153 A1 | 8/2009 | Shriver |
| 2009/0198216 A1 | 8/2009 | Muni et al. |
| 2009/0216196 A1 | 8/2009 | Drontle et al. |
| 2009/0240112 A1 | 9/2009 | Goldfarb et al. |
| 2009/0240237 A1 | 9/2009 | Goldgarb et al. |
| 2009/0312745 A1 | 12/2009 | Goldfarb et al. |
| 2009/0326450 A1 | 12/2009 | Ostrovsky et al. |
| 2010/0010309 A1 | 1/2010 | Kitagawa |
| 2010/0030113 A1 | 2/2010 | Morriss et al. |
| 2010/0042046 A1 | 2/2010 | Chang et al. |
| 2010/0076269 A1 | 3/2010 | Makower et al. |
| 2010/0099946 A1 | 4/2010 | Jenkins et al. |
| 2010/0106141 A1 | 4/2010 | Osypka et al. |
| 2010/0114066 A1 | 5/2010 | Makower et al. |
| 2010/0168511 A1 | 7/2010 | Muni et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0211007 A1 | 8/2010 | Lesch, Jr. et al. |
| 2010/0217261 A1 | 8/2010 | Watson |
| 2010/0240950 A1 | 9/2010 | Heimberger |
| 2010/0262075 A1 | 10/2010 | Danitz et al. |
| 2010/0268087 A1 | 10/2010 | Hirota |
| 2010/0268245 A1 | 10/2010 | Chang et al. |
| 2010/0274188 A1 | 10/2010 | Chang et al. |
| 2010/0280316 A1 | 11/2010 | Dietz et al. |
| 2010/0298862 A1 | 11/2010 | Chang et al. |
| 2010/0331776 A1 | 12/2010 | Salahieh et al. |
| 2011/0004057 A1 | 1/2011 | Goldfarb et al. |
| 2011/0009700 A1 | 1/2011 | Ostrovsky et al. |
| 2011/0040269 A1 | 2/2011 | Cline |
| 2011/0060214 A1 | 3/2011 | Makower |
| 2011/0071349 A1 | 3/2011 | Drontle et al. |
| 2011/0112476 A1 | 5/2011 | Kauphusman et al. |
| 2011/0112512 A1 | 5/2011 | Muni et al. |
| 2011/0160740 A1 | 6/2011 | Makower et al. |
| 2011/0190831 A1 | 8/2011 | Mafi et al. |
| 2011/0218492 A1 | 9/2011 | McDaniel et al. |
| 2011/0224647 A1 | 9/2011 | Lazarus |
| 2011/0224652 A1 | 9/2011 | Drontle et al. |
| 2011/0264134 A1 | 10/2011 | Drontle et al. |
| 2011/0288477 A1 | 11/2011 | Ressemann et al. |
| 2011/0313392 A1 | 12/2011 | Varghese et al. |
| 2012/0010646 A1 | 1/2012 | Keith et al. |
| 2012/0046664 A1 | 2/2012 | McGuckin, Jr. et al. |
| 2012/0071824 A1 | 3/2012 | Chang et al. |
| 2012/0101441 A1 | 4/2012 | Sargent, Jr. |
| 2012/0116254 A1 | 5/2012 | Morriss |
| 2012/0136207 A1 | 5/2012 | Goldfarb et al. |
| 2012/0162401 A1 | 6/2012 | Melder et al. |
| 2012/0172912 A1 | 7/2012 | Ressemann et al. |
| 2012/0184983 A1 | 7/2012 | Chang et al. |
| 2012/0190973 A1 | 7/2012 | Ressemann et al. |
| 2012/0197240 A1 | 8/2012 | Smith et al. |
| 2012/0238952 A1 | 9/2012 | Mitchell et al. |
| 2012/0245419 A1 | 9/2012 | Makower et al. |
| 2012/0265055 A1 | 10/2012 | Melsheimer et al. |
| 2012/0265094 A1 | 10/2012 | Goldfarb et al. |
| 2012/0283625 A1 | 11/2012 | Keith et al. |
| 2013/0041314 A1 | 2/2013 | Dillon |
| 2013/0046138 A1 | 2/2013 | McLawhorn |
| 2013/0096384 A1 | 4/2013 | Arai |
| 2013/0096605 A1 | 4/2013 | Becker |
| 2013/0103004 A1 | 4/2013 | Gray et al. |
| 2013/0137920 A1 | 5/2013 | Schaeffer et al. |
| 2013/0226146 A1 | 8/2013 | Tekulve |
| 2013/0238003 A1 | 9/2013 | Fischer et al. |
| 2014/0088355 A1 | 3/2014 | Schaeffer |
| 2014/0107413 A1 | 4/2014 | Tremaglio et al. |
| 2014/0243615 A1 | 8/2014 | Schaeffer et al. |
| 2015/0246205 A1 | 9/2015 | Schaeffer |
| 2016/0302650 A1 | 10/2016 | Melder et al. |
| 2018/0028783 A1 | 2/2018 | Dillon et al. |
| 2018/0256012 A1 | 9/2018 | Frey et al. |

FOREIGN PATENT DOCUMENTS

| | | |
|---|---|---|
| EP | 0163266 | 12/1985 |
| EP | 2368481 | 9/2011 |
| EP | 2522386 | 11/2012 |

(56) References Cited

FOREIGN PATENT DOCUMENTS

| | | |
|---|---|---|
| EP | 2710949 | 3/2014 |
| GB | 2465621 | 6/2010 |
| WO | WO98043530 | 10/1998 |
| WO | WO2001026726 | 4/2001 |
| WO | WO200170308 | 9/2001 |
| WO | WO2003001986 | 1/2003 |
| WO | WO2006020180 | 2/2006 |
| WO | WO2008045242 | 4/2008 |
| WO | WO2011082074 | 7/2011 |
| WO | WO2011084655 | 7/2011 |
| WO | WO2014134257 | 9/2014 |
| WO | WO2017075574 | 5/2017 |
| WO | WO2017136347 | 8/2017 |

OTHER PUBLICATIONS

EyeMAX CCD Laparscopes [online brochure]. Richard Wolf GmbH [retrieved Nov. 15, 2013]. Retrieved from the internet: URL: http://www.richard-wolf.com/uploads/media/A_658_Eyemax_GB_I07.pdf. pp. 1-8.

EyeMAX Flexible LED Cystoscope [online brochure]. Richard Wolf GmbH [retrieved Nov. 15, 2013]. Retrieved from the internet: URL: http://www.richardwolfusa.com/fileadmin/images/content/USA_data/PDF_documents/Urology/Flexible_LED_Digital_Cystoscope_brochure_01312013.pdf. pp. 1-4.

Olympus Naso-laryngoscopes. Olympus. Retrieved from the internet: URL: www.olympuskeymed.com, pp. 1-3.

XprESS Multi-Sinus Dilation Tool Using Bending Tool. Instructions for Use, Entellus Medical, Sep. 2011, pp. 1-7.

XprESS Multi-Sinus Dilation Tool. Instructions for Use, Entellus Medical, May 2011, pp. 1-7.

A trial study of RhinoSleep for the diagnosis of sleep apnea. Psychiatry and Clinical Neurosciences. Jun. 2001, pp. 1-2.

E.G. Scan—Trans-nasal, disposable system for upper GI screening [online brochure]. SynMed Ltd. [retrieved Jun. 4, 2014]. Retrieved from the internet: URL: http://www.synmed.co.uk/products/eg_scan/pdf/SynMed_E.G.Scan_Brochure.pdf.

Drug-induced Sleep Endoscopy webpage [online], Eric J. Kezirian [retrieved Nov. 14, 2013]. Retrieved from the internet: URL: http://www.sleep-doctor.com/surgical-treatment-overview/drug-induced-sleep-endoscopy/.

EyeMax webpage [online], Richard Wolf [retrieved Nov. 14, 2013]. Retrieved from the internet: URL: http://www.richard-wolf.com/en/human-medicine/visualisation/video-endoscopes/ccd-endoscopes.html.

European Patent Office, Extended European Search Report, for International Application No. 13185810.2, dated Jan. 7, 2014, pp. 1-5.

International Searching Authority. International Search Report and Written Opinion, for International App. No. PCT/US2014/018878. dated Jun. 11, 2014. p. 1-12.

European Patent Office, European Search Report for application No. 12194127.2 dated Apr. 9, 2013, p. 1-5.

European Patent Office, European Extended Search Report for application No. 12194127.2 dated Jul. 25, 2013, p. 1-8.

European Patent Office, Examination Report for European Patent Application No. 12194127.2, dated Jan. 19, 2018, pp. 1-4.

International Bureau of WIPO, "International Report on Patentability," for Int. App. No. PCT/US2014/018878, dated Sep. 11, 2015, pp. 1-9.

Japanese Patent Office, English Translation of Office Action for Japanese Patent Application No. 2015-560297, dated Oct. 31, 2017, p. 1-5.

Richard Wolf GmbH, Flexible sensor endoscopes for the ENDOCAM Logic 4K, Online brochure, as viewed on Mar. 21, 2019, p. 1-9, Germany.

Richard Wolf GmbH, Flexible sensor endoscopes for the ENDOCAM Logic 4K Camera Platform, Online brochure, as viewed on Mar. 21, 2019, p. 1-12, Germany.

* cited by examiner

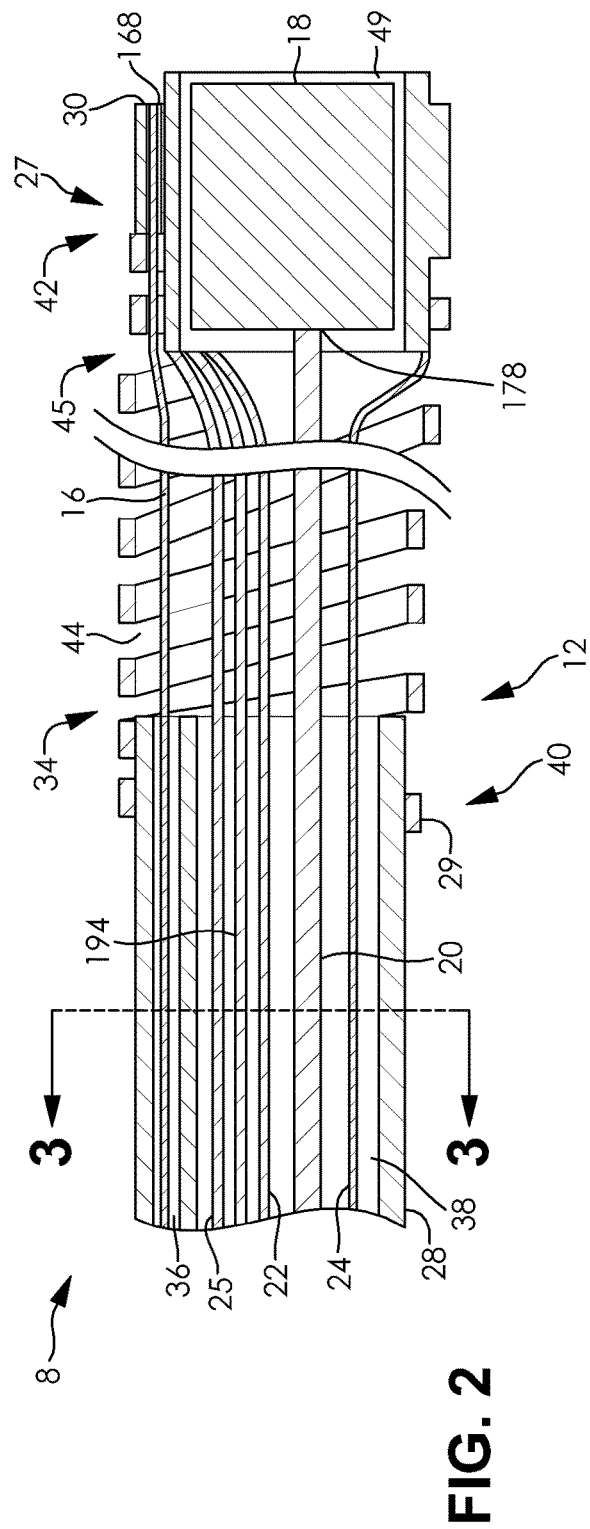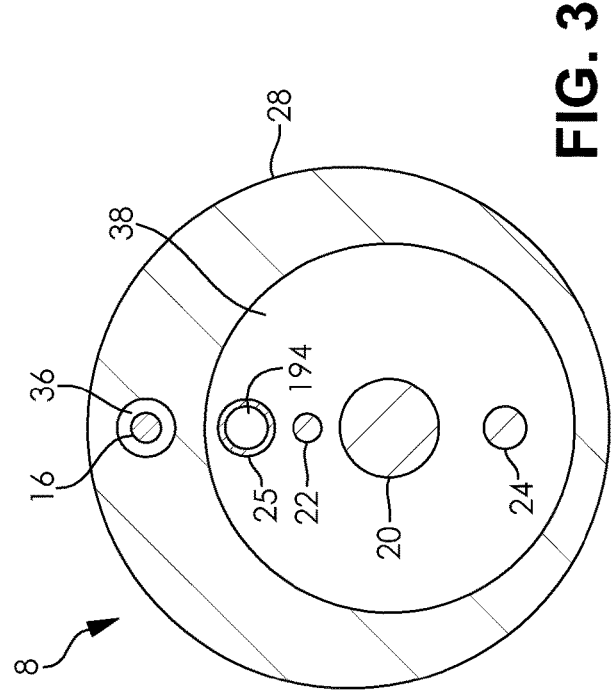

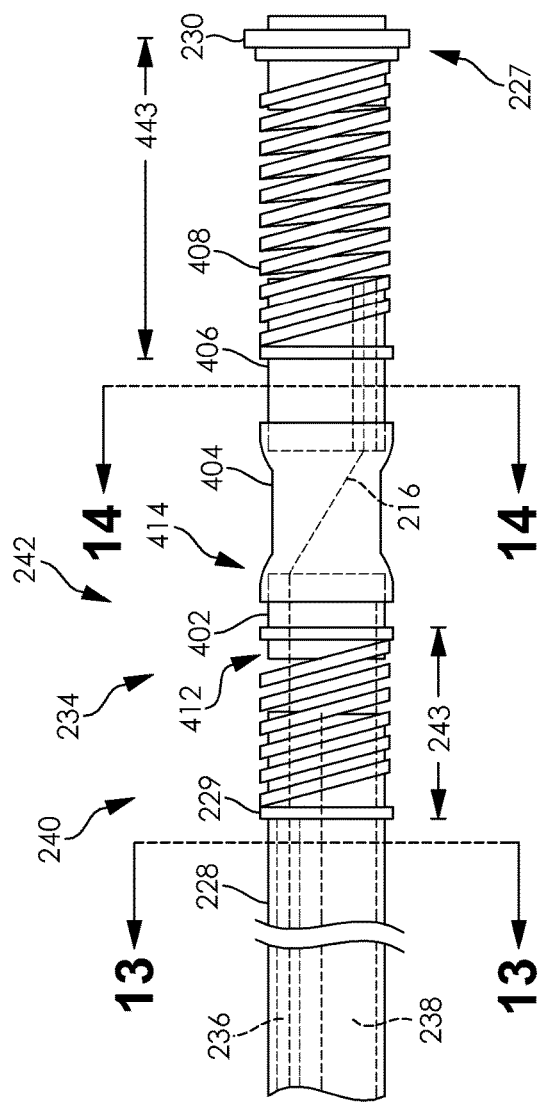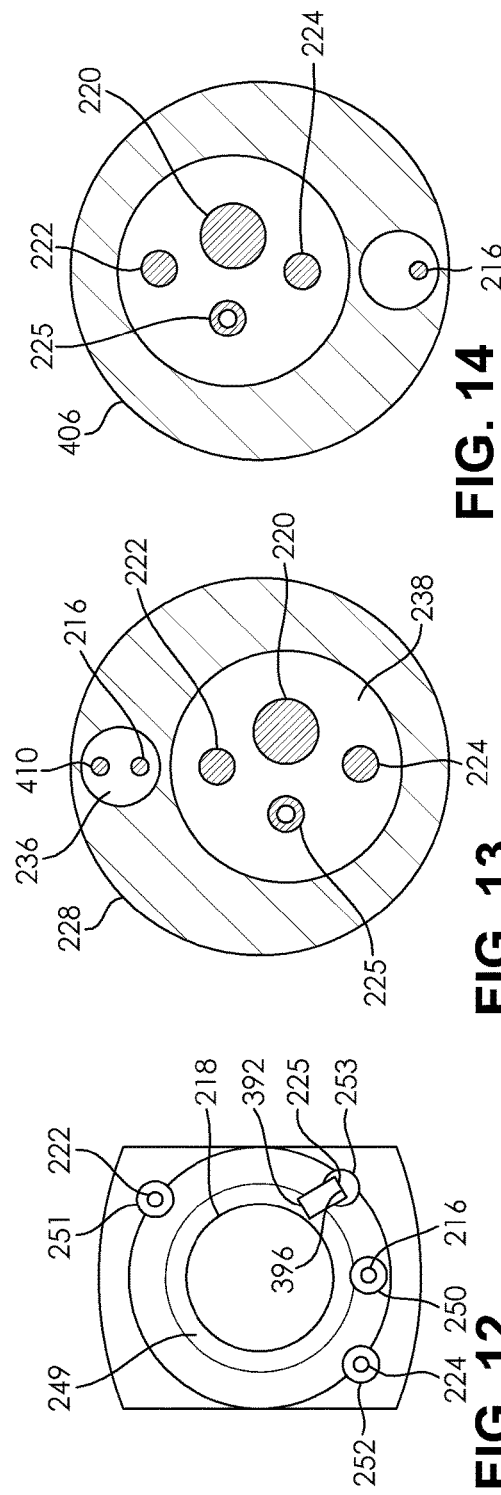
FIG. 11
FIG. 12
FIG. 13
FIG. 14

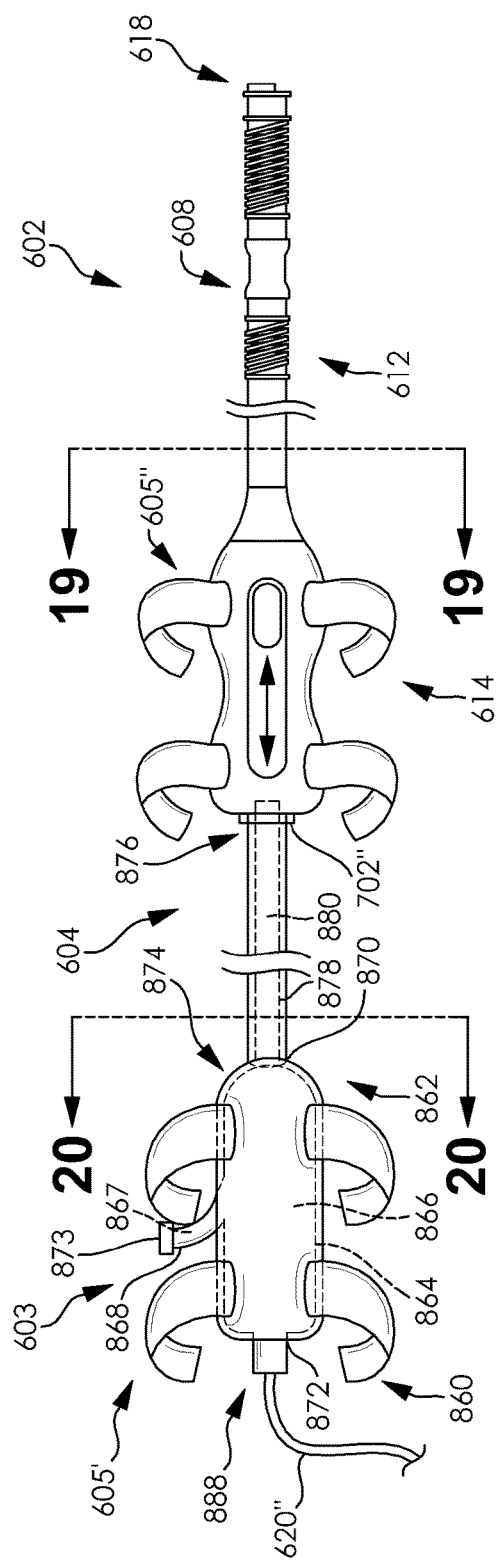

DEFLECTABLE CATHETERS, SYSTEMS, AND METHODS FOR THE VISUALIZATION AND TREATMENT OF BODILY PASSAGES

RELATED APPLICATIONS

This application is a continuation of U.S. patent application Ser. No. 14/633,561, filed on Feb. 27, 2015, and which claims the benefit of U.S. Provisional Application No. 61/946,231, filed Feb. 28, 2014. The entire contents of each of these related applications is incorporated into this disclosure by reference.

FIELD

The disclosure relates generally to medical devices, systems, and methods. More particularly, the disclosure relates to medical devices, systems, and methods for the visualization and treatment of bodily passages, such as an airway, sinus cavity, or sinus passage.

BACKGROUND

Obstructive Sleep Apnea (OSA) Syndrome is a respiratory disorder characterized by periodic cessation of breathing caused by upper airway obstruction. Sleep causes the muscles of the upper airway to relax and the associated soft tissue to sag, resulting in narrowing or collapse of the upper airway, and consequent reduction in ventilation. Mild OSA can lead to fatigue, reduced alertness following sleep, and a general reduction in productivity for the affected individual. Severe OSA can lead to sleep deprivation, hypoxemia, and depression.

OSA can have several causes, with each requiring a different remedy. For example, in some cases OSA can be the result of obesity and/or diabetes. In other cases, OSA is caused by the anatomy of the septum, turbinates, palate, tongue, pharyngeal wall, muscle tone in upper airway, epiglottis, and/or uvula. Therefore, individual treatment of OSA requires a study of the causes of OSA in the individual to determine the appropriate form of treatment.

The conventional approach to diagnosis of sleep disorders, such as OSA, has been to require an individual to participate in a "sleep study," which is completed during natural sleep or artificially induced sleep. During a natural sleep study, the individual is outfitted with an array of sensors attached to the surface of the body and face that monitor the individual's respiration, pulse, and blood oxygen saturation, among other physiological statistics. During a drug induced sleep endoscopy (DISE), during which sleep is artificially induced using midazolam or propofol, a scope is disposed within the airway to determine the source of the obstruction.

Conventional sleep studies, however, have several shortcomings. For example, during natural sleep studies visualization of the airway is not performed, which prevents identifying potential obstructions. Artificially induced sleep studies require the use of anesthesia, which increases the risks associated with performing the study. In addition, inducing artificial sleep may alter the results of the sleep study due to the sleep-inducing drug manipulating normal bodily functions. For example, the structural configuration and function of an airway may be altered when using sleep-inducing drugs as compared to the structural configuration and function of an airway during normal sleep. Moreover, artificially induced sleep studies are typically performed with the individual laying on his or her back, which fails to provide data regarding obstructions when the individual is in other sleeping position.

Therefore, a need exists for improved medical devices, systems, and methods for visualizing and treating bodily passages.

BRIEF SUMMARY OF SELECTED EMBODIMENTS

An example embodiment of a deflectable catheter that has a lengthwise axis comprises a handle, an elongate member, and a wire member. The handle has an actuator that is moveable between an actuator first position and an actuator second position. The elongate member comprises a first shaft, a first flexible member, a second shaft, a tubular member, a third shaft, a second flexible member, and a cap. The elongate member is moveable between a substantially straight configuration when the actuator is in the actuator first position and a curved configuration when the actuator is in the actuator second position. The first shaft is attached to the handle and defines a first lumen and a second lumen. The first flexible member is attached to the first shaft and has a proximal end, a distal end, and defines a passageway in communication with each of the first lumen and second lumen defined by the first shaft. The second shaft is attached to the first flexible member and defines a first lumen and a second lumen. Each of the first lumen and second lumen defined by the second shaft is in communication with the passageway defined by the first flexible member. The first lumen defined by the second shaft is disposed on a second shaft lengthwise axis that is parallel to the lengthwise axis of the deflectable catheter. The tubular member is attached to the second shaft and defines a lumen in communication with each of the first lumen and second lumen defined by the second shaft. The third shaft is attached to the tubular member and defines a first lumen and a second lumen. Each of the first lumen and second lumen defined by the third shaft is in communication with the lumen defined by the tubular member. The second lumen defined by the third shaft is disposed on a third shaft lengthwise axis that is parallel to the lengthwise axis of the deflectable catheter. The second flexible member is attached to the third shaft and has a proximal end, a distal end, and defines a passageway in communication with each of the first lumen and second lumen defined by the third shaft. The cap is attached to the second flexible member. The wire member has a first end attached to the actuator and a second end attached to the elongate member. The wire member extends from the first end through the first lumen defined by the first shaft, through the passageway defined by the first flexible member, through the first lumen defined by the second shaft, through the lumen defined by the tubular member, through the second lumen defined by the third shaft, and through the passageway defined by the second flexible member. The second shaft lengthwise axis and the third shaft lengthwise axis are opposably positioned relative to the lengthwise axis of the deflectable catheter.

An example embodiment of a deflectable catheter system comprises a proximal housing, a deflectable catheter, and a tubular member. The tubular member is attached to the proximal housing and the deflectable catheter. The proximal housing has a proximal end, a distal end, and a body that defines a chamber, an irrigation port, a first opening, and a second opening. The irrigation port has a passageway and an end. The passageway of the irrigation port is in communication with the chamber defined by the proximal housing and the end of the irrigation portion has a connector. The deflectable catheter has an elongate member, a handle, a wire member, an imaging device, a data transfer cable, a first optical fiber, a second optical fiber, and an irrigation tube. The handle has a first opening, a second opening, and a chamber in communication with the first opening and the second opening defined by the handle. The tubular member has a proximal end, a distal end, and a body that defines a lumen that extends from the proximal end to the distal end of the tubular member. The proximal end of the tubular member is attached to the proximal housing such that the lumen defined by the tubular member is in communication with the chamber defined by the proximal housing. The distal end of the tubular member is attached to the handle of the deflectable catheter such that the lumen defined by the tubular member is in communication with the chamber defined by the handle.

An example method of visualizing a bodily passage comprises the steps of: introducing a deflectable catheter that has a deflectable catheter proximal end and a deflectable catheter distal end into a bodily passage such that the deflectable catheter distal end is disposed in the bodily passage, the deflectable catheter comprises an elongate member, an actuator, and a wire member; advancing the actuator from an actuator first position to an actuator second position such that a curve is defined along the length of the elongate member and within the bodily passage; allowing an interval of time to pass; advancing the actuator from the actuator second position to the actuator first position; removing the deflectable catheter from the bodily passage.

DESCRIPTION OF FIGURES

FIG. 2 is a partial sectional view of the deflectable catheter illustrated in FIG. 1, taken along the lengthwise axis of the deflectable catheter.

FIG. 3 is a sectional view of the deflectable catheter illustrated in FIG. 1, taken along line 3-3.

FIG. 11 is a partial side view of the deflectable catheter illustrated in FIG. 10.

FIG. 12 is an end view of the distal end of the deflectable catheter illustrated in FIG. 10.

FIG. 13 is a sectional view of the deflectable catheter illustrated in FIG. 11, taken along line 13-13.

FIG. 14 is a sectional view of the deflectable catheter illustrated in FIG. 11, taken along line 14-14.

FIG. 18 is a partial top view of a deflectable catheter system.

FIG. 19 is a sectional view of the deflectable catheter system illustrated in FIG. 18, taken along line 19-19.

FIG. 20 is a sectional view of the deflectable catheter system illustrated in FIG. 18, taken along line 20-20.

FIG. 21 is a sectional view of another deflectable catheter system.

DESCRIPTION OF EMBODIMENTS

Figure 1:
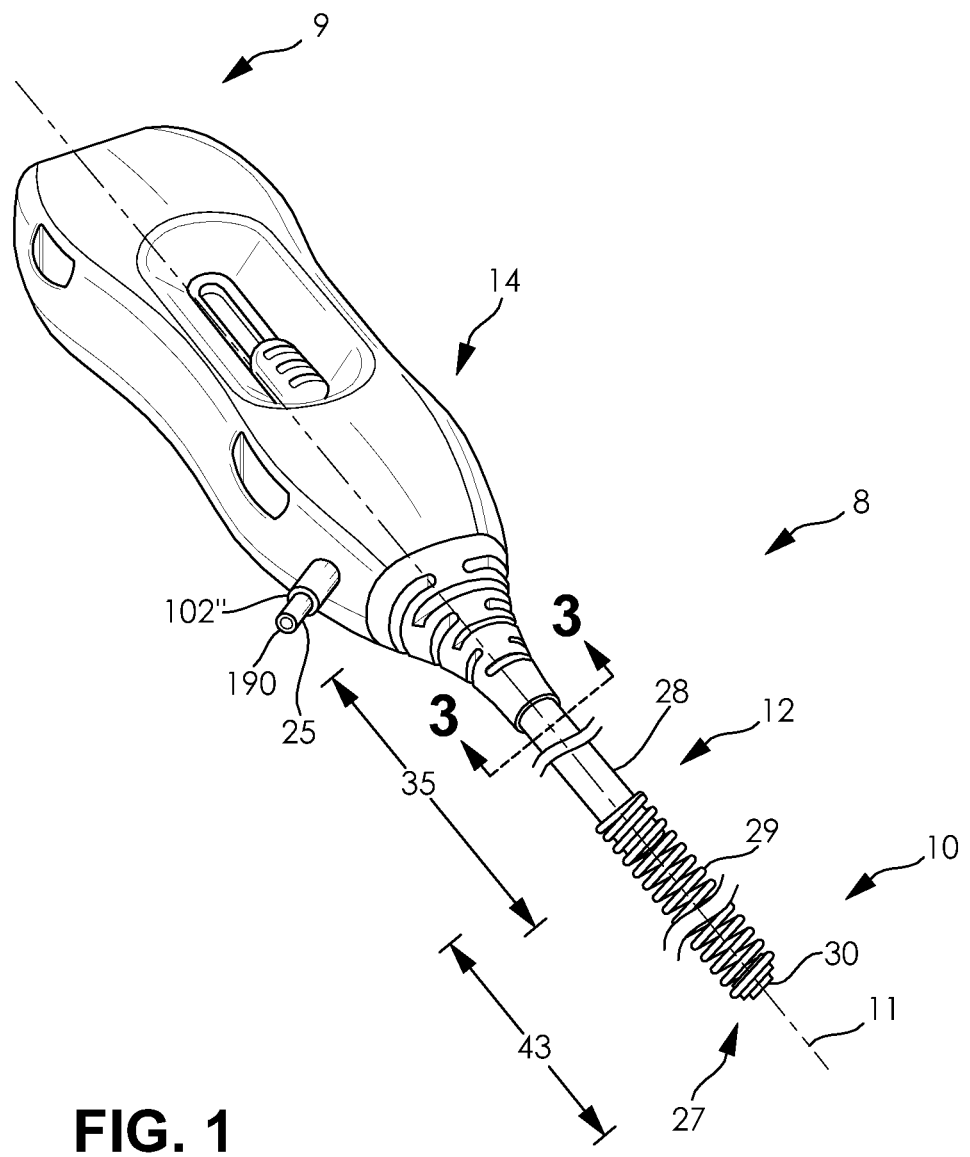
FIG. 1 is a perspective view of a deflectable catheter in a first configuration.

The following detailed description and the appended drawings describe and illustrate various example embodiments of deflectable catheters, deflectable catheter systems, methods of visualizing and/or treating a bodily passage using a deflectable catheter, and methods of visualizing and/or treating a bodily passage using a deflectable catheter system. The description and illustration of these examples are provided to enable one skilled in the art to make and use a deflectable catheter, deflectable catheter system, practice a method of visualizing and/or treating a bodily passage using a deflectable catheter, and to practice a method of visualizing and/or treating a bodily passage using a deflectable catheter system according to an embodiment. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The term "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The term "diameter" refers to the length of a straight line passing from side to side through the center of a body, element, or feature, and does not impart any structural configuration on the body, element, or feature. The term "circumference" refers to a displacement measured along the exterior surface area of a body, element, or feature and does not impart any structural configuration on the body, element, or feature. The use of "bodily passage" or "body passage" refers to any passage within the body of an animal, including, but not limited to, humans, and includes, but is not limited to, elongate passages. The term "sinus passage" refers to the nasal passages, and includes, but is not limited to, eustachian tube(s), primary ostium, accessory ostium, and/or an opening defined by a ventilation tube. The term "airway" refers to any airway including, but not limited to, the nasal cavity, nasopharynx, oropharynx, pharynx, trachea, bronchial tubes, esophagus, and/or lungs. The term "sinus cavity" refers to the frontal, ethmoid, sphenoid, and/or maxillary sinus.

FIGS. 1, 2, 3, 4, 5, 5A, 6, 7, 8, and 9, illustrate a deflectable catheter 8 that has a proximal end 9, a distal end 10, and a lengthwise axis 11. The deflectable catheter 8 includes an elongate member 12, a handle 14, a wire member 16, an imaging device 18, a data transfer cable 20, a first optical fiber 22, a second optical fiber 24, and an irrigation tube 25.

Elongate member 12 can have any suitable outside diameter and any suitable length, and skilled artisans will be able to select a suitable outside diameter and length for an elongate member according to a particular embodiment based on various considerations, including the desired bodily passage within which a deflectable catheter is intended to be used. Example lengths considered suitable for an elongate member include lengths between 60 centimeters and 150 centimeters, lengths between about 60 centimeters and about 150 centimeters, and any other length considered suitable for a particular embodiment. Example outside diameters considered suitable for an elongate member include outside diameters between 1.0 millimeter and 8.0 millimeters, between about 1.0 millimeter and about 8.0 millimeters, between 2.0 millimeters and 6.0 millimeters, between about 2.0 millimeters and about 6.0 millimeters, between 3.0 millimeters and 5.0 millimeters, between about 3.0 millimeters and about 5.0 millimeters, equal to, substantially equal to, or about 4.0 millimeters, outside diameters less than, or equal to, 4.0 millimeters, and any other outside diameter considered suitable for a particular embodiment.

The elongate member 12, and the components that form the elongate member 12 (e.g., shaft, flexible member, tubular member), can be formed of any suitable material and can be fabricated using any suitable method of manufacture. Skilled artisans will be able to select a suitable material to form an elongate member, or a component that forms a portion of an elongate member (e.g., shaft, flexible member, tubular member), and a suitable method of manufacture according to a particular embodiment based on various considerations, including the desired flexibility of the elongate member. Example materials considered suitable to form an elongate member, or a component that forms a portion of an elongate member (e.g., shaft, flexible member, tubular member), include biocompatible materials, materials that can be made biocompatible, metals such as stainless steel, titanium, nickel-titanium alloy (e.g., Nitinol), polymers, Pebax (Pebax is a registered trademark of AtoChimie Corporation of Allee des Vosges, Courbevoie, France), nylon, polyethylene, polyurethane, silicone, coiled materials, braided materials, and any other material considered suitable for a particular application. Example methods of manufacture considered suitable to fabricate an elongate member, or a component that forms a portion of an elongate member (e.g., shaft, flexible member, tubular member), include extrusion processes, molding processes, and any other method considered suitable for a particular application.

Figure 7:
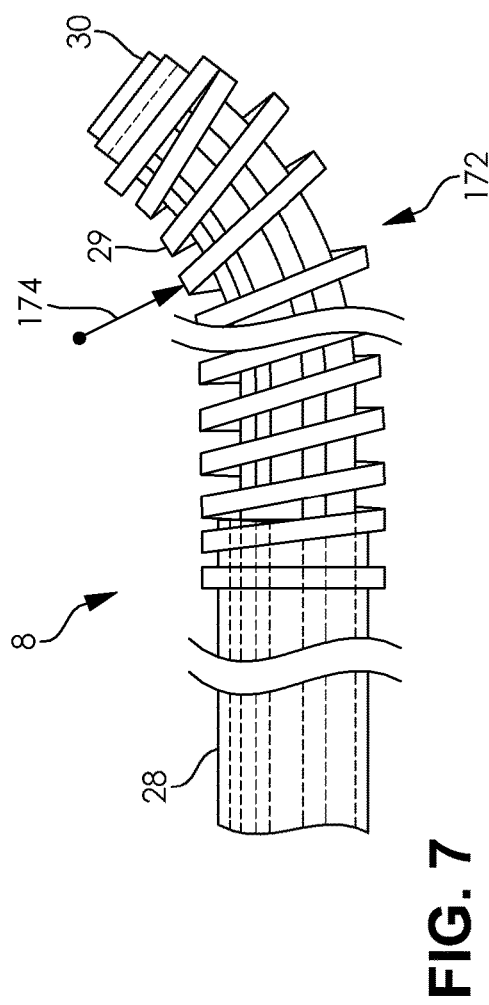
FIG. 7 is a partial side view of the deflectable catheter illustrated in FIG. 1 in a second configuration.

In the illustrated embodiment, elongate member 12 has a proximal end 26, a distal end 27, a first shaft 28, a first flexible member 29, and a cap 30. Elongate member 12 has a first, straight, configuration, as shown in FIG. 1, and a second, curved, configuration, as shown in FIG. 7. The first configuration is different than the second configuration. While the elongate member 12 has been illustrated as being straight in the first configuration, an elongate member can have any suitable configuration in the first configuration, such as substantially straight, or partially straight.

The first shaft 28 has a proximal end 32, a distal end 34, a length 35, and a body that defines a first lumen 36 and a second lumen 38. The length 35 extends from the proximal end 32 to the distal end 34 of the first shaft 28. Each of the first lumen 36 and the second lumen 38 extends from the proximal end 32 of the first shaft 28 to the distal end 34 of the first shaft 28. The first lumen 36 has a diameter that is less than the diameter of the second lumen 38 and is sized and configured to receive a portion of the wire member 16. The second lumen 38 is sized and configured to receive a portion of the imaging device 18, data transfer cable 20, first optical fiber 22, second optical fiber 24, and/or irrigation tube 25. Alternatively, the first lumen and/or second lumen defined by a shaft can be sized and configured to receive devices in addition to, or alternative to, those described herein.

While the body of the first shaft 28 has been illustrated as defining a first lumen 36 and a second lumen 38, the body of the shaft of a deflectable catheter can define any suitable number of lumens, and skilled artisans will be able to select a suitable number of lumens for the body of a shaft to define according to a particular embodiment based on various considerations, including the number of curves intended to be defined by an elongate member when it is in the second configuration. Example number of lumens considered suitable for the body of a shaft to define include one, at least one, two, a plurality, three, four, five, six, and any other number considered suitable for a particular application.

The first flexible member 29 is attached to the distal end 34 of the first shaft 28 and has a proximal end 40, a distal end 42, a length 43, and defines a passageway 44. The length 43 of the first flexible member 29 extends from the proximal end 40 to the distal end 42 of the first flexible member 29. In the embodiment shown, the proximal end 40 of the first flexible member 29 is disposed over a portion of the exterior surface of the first shaft 28 and is attached to first shaft 28 using an adhesive. However, alternative embodiments can include a first flexible member that is formed as a distal portion of a shaft, attached to the distal end of the first shaft, or embedded within the material that forms the first shaft. The passageway 44 defined by the first flexible member 29 is in communication with each of the first lumen 36 and second lumen 38 defined by the first shaft 28. In the embodiment illustrated, the length 35 of the first shaft 28 is greater than the length 43 of the first flexible member 29. However, alternative embodiments can include a first shaft that has a length than is less than, equal to, or substantially equal to, the length of a first flexible member.

The first flexible member 29 (e.g., localized flexible region) is relatively more flexible than the first shaft 28. Any suitable structure and/or material can be used to form a flexible member of an elongate member. Skilled artisans will be able to select a suitable structure and material to form a flexible member of an elongate member according to a particular embodiment based on various considerations, including the degree of curvature intended to be achieved when the deflectable catheter is in a second configuration. In the illustrated embodiment, the first flexible member 29 is a compression spring (e.g., medical grade compression spring) that defines a helical configuration that extends from the proximal end 40 of the first flexible member 29 to the distal end 42 of the first flexible member 40. The use of a compression spring provides a mechanism for returning the elongate member 12 to its first, straight, configuration after it has achieved a second, curved, configuration. Alternative structures and/or materials considered suitable to form a flexible member include helical cut nickel-titanium alloy (e.g., Nitinol) segments, helical cut polymer segments, malleable materials that can be customized and/or shaped by a user using his or her hands, or another device, prior to, or during, the performance of a procedure, and any other structure and/or material considered suitable for a particular embodiment. A flexible member can be formed of any material capable of moving between first and second configurations and returning to its first configuration when no force is being applied to the flexible member.

Optionally, the first flexible member of an elongate member, or any flexible member of an elongate member, can comprise a localized flexible region of the elongate member that is relatively more flexible than different regions of the elongate member. The localized flexible region of the elongate member can extend along the entire circumference, or a portion of the circumference of the elongate member and between the proximal end of the elongate member and the distal end of the elongate member, from the proximal end of the elongate member toward the distal end of the elongate member, or from the distal end of the elongate member toward the proximal end of the elongate member. Some embodiments can also include more than one, or a plurality of, localized flexible regions (e.g., elongate member 212). A localized flexible region of an elongate member can comprise any suitable structure and/or material capable of forming a first region of an elongate member that it is relatively more flexible than a second region of the elongate member that is different than the first region (e.g., shaft, flexible member). Skilled artisans will be able to select a suitable structure and/or material to form a localized flexible region according to a particular embodiment based on various considerations, including the desired flexibility intended to be imparted on the localized flexible region. Example materials considered suitable to form a localized flexible region of an elongate member include the materials that form an elongate member, helical cut nickel-titanium alloy (e.g., Nitinol) segments, helical cut polymer segments, malleable materials that can be customized and/or shaped by a user using his or her hands, or another device, prior to, or during, the performance of a procedure, and any other structure and/or material considered suitable for a particular embodiment. A localized flexible region can be formed of any material capable of moving between first and second configurations. For example, a shaft of an elongate member can be formed of a first material and the localized flexible region of the elongate member can be formed of a second material. The first material can be the same as, or different than, the second material. For example, the first material can have a first durometer hardness and the second material can have a second durometer harness that is less than the first durometer harness. Optionally, a localized flexible region can comprise a portion of the elongate member that has a cross-sectional surface area that is less than other regions of the elongate member that are different than the localized flexible regions (e.g., shaft). Optionally, an elongate member can be a continuous piece of material such that any localized flexible regions included on the elongate member can be formed by the material that forms the elongate member (e.g., helical cut portions of elongate member, recesses). Optionally, a localized flexible region can comprise one or more reliefs (e.g., recesses, notches, cuts) defined on a portion of the elongate member.

As shown in FIG. 2., the cap 30 is attached to the distal end 42 of the first flexible member 29. As best illustrated in FIGS. 4, 5, 5A, and 6, the cap 30 has a lengthwise axis 30', a proximal end 45, a distal end 46, and a body that defines a shaft 47, a first shaft opening 47', a second shaft opening 47", a flange 48, a passageway 49, a wire member opening 50, a first optical fiber opening 51, a second optical fiber opening 52, and an irrigation opening 53. In the embodiment shown, the proximal end 45 of the cap 30 is disposed within the passageway 44 defined by the first flexible member 29 and is attached to first flexible member 29 using an adhesive. However, alternative embodiments can include a cap that is attached to the distal end of the first flexible member, or embedded within the material that forms the first flexible member. Optionally, a cap can be omitted from an elongate member and the various elements and features described as being attached to a cap can be attached to the distal end, or a distal portion, of a flexible member, tubular member, or dual lumen shaft.

The shaft 47 extends from the proximal end 45 of the cap 30 to the flange 48 and has a length 47''' and a first outside diameter 49'. The flange 48 extends from the shaft 47 and away from the lengthwise axis 30' of the cap 30 and has a length 48' and a second outside diameter 51'. The length 48' of the flange 48 is less than the length 47''' of the shaft 47. The second outside diameter 51' of the flange 48 is greater than the first outside diameter 49' of the shaft 47. The passageway 49 extends through the shaft 47 and the flange 48, from the proximal end 45 of the cap 30 to the distal end 46 of the cap 30, and is sized and configured to receive a portion of imaging device 18 and/or data transfer cable 20. Each of the wire member opening 50, first optical fiber opening 51, second optical fiber opening 52, and irrigation opening 53 extends through the length 48' of the flange 48. The wire member opening 50 is sized and configured to receive a portion of wire member 16 such that the wire member 16 can be attached to the cap 30 within the wire member opening 50. The first optical fiber opening 51 is sized and configured to receive a portion of first optical fiber 22 such that the first optical fiber 22 can be attached to the cap 30 within the first optical fiber opening 51. The second optical fiber opening 52 is sized and configured to receive a portion of the second optical fiber 24 such that the second optical fiber 24 can be attached to the cap 30 within the second optical fiber opening 52. The irrigation opening 53 is sized and configured to receive a portion of the irrigation tube 25 such that the irrigation tube 25 can be attached to the cap 30 within the irrigation opening 53.

Each of the first shaft opening 47' and second shaft opening 47" is defined between the proximal end 45 of the cap 30 and the flange 48 and provides access to the passageway 49. Each of the first shaft opening 47' and second shaft opening 47" is sized and configured to allow securement of the imaging device 18 to the cap 30 using any suitable form of attachment, such as those described herein. For example, each of the first shaft opening 47' and second shaft opening 47" can be sized and configured to allow an adhesive to be passed through each of the openings such that the imaging device 18 can be attached to the cap 30.

In the embodiment shown, the first outside diameter 49' of the shaft 47 is sized and configured to be received by the passageway 44 defined by the first flexible member 29. In the embodiment illustrated, the shaft 47 is entirely disposed within the passageway 44 defined by the first flexible member 29 such that the flange 48 is adjacent to, and contacts, the distal end 42 of the first flexible member 29. Alternatively, the shaft 47 can be partially disposed within a passageway defined by a flexible member such that the flange does not contact the flexible member.

While cap 30 has been illustrated as having a particular structural configuration, a cap can have any suitable structural configuration and the illustrated cap 30 is merely an example of a suitable configuration of a cap. Skilled artisans will be able to select a suitable structural configuration for a cap according to a particular embodiment based on various considerations, including the structural configuration of the lumen in which a portion of the cap is intended to be disposed. Example structural configurations considered suitable for a cap include caps that define a passageway (e.g., passageway 49) that has an inside diameter between about 1.790 millimeters and about 1.830 millimeters, caps that define a passageway (e.g., passageway 49) that has an inside diameter equal to, substantially equal to, or about 1.810 millimeters, caps that define a wire member opening (e.g., wire member opening 50) equal to, substantially equal to, or about 0.356 millimeters, caps that define an optical fiber opening (e.g., first optical fiber opening 51, second optical fiber opening 52), and/or a irrigation opening (e.g., irrigation opening 53) equal to, substantially equal to, or about 0.55 millimeters, caps that have a length from the proximal end of the cap to the distal end of the cap equal to, substantially equal to, or about 6.2 millimeters, caps that define a shaft opening (e.g., first shaft opening 47', second shaft opening 47") equal to, substantially equal to, or about 0.80 millimeters, and any other configuration considered suitable for a particular embodiment.

While the first flexible member 29 has been described as being adhesively attached to the first shaft 28 and the cap 30 has been described as being adhesively attached to the first flexible member 29, a flexible member can be attached to a shaft and a cap can be attached to a flexible member using any suitable structure for, or method of, attachment between two components. Skilled artisans will be able to select a suitable structure for, or method of, attachment between a flexible member and a shaft and between a cap and a flexible member according to an embodiment based on various considerations, including the materials that form the shaft, flexible member, and/or cap. Example structures for, and methods of, attachment between a shaft and a flexible member and between a cap and a flexible member considered suitable include using an adhesive, welding, fusing (e.g., heat fusing), using threaded connections, and any other structure for, or method of, attachment between two components considered suitable for a particular embodiment.

While the imaging device 18 has been described as being adhesively attached to the first flexible member 29, an imaging device can be attached to a flexible member using any suitable structure for, or method of, attachment between two components. Skilled artisans will be able to select a suitable structure for, or method of, attachment between an imaging device and a flexible member according to an embodiment based on various considerations, including the materials that form the imaging device and/or the flexible member. Example structures for, and methods of, attachment between an imaging device and a flexible member considered suitable include using an adhesive, welding, fusing (e.g., heat fusing), using threaded connections, and any other structure for, or method of, attachment between two components considered suitable for a particular embodiment.

Optionally, an elongate member can include a safety wire to prevent overextension of the elongate member and/or flexible member during use. For example, a safety wire that has a first end attached to the distal end of the first shaft and a second end attached to the cap can be included in a deflectable catheter. The safety wire can be formed of any suitable material and have any suitable structural configuration. Example materials considered suitable to form a safety wire include stainless steel, polymers, and any other material considered suitable for a particular embodiment. Example structural configurations considered suitable for a safety wire include cross-sectional configurations that are round, rectangular (e.g., flat wire), and any other structural configuration considered suitable for a particular embodiment. While the optional safety wire has been described as being attached at particular locations on an elongate member, a safety wire can be attached at any suitable location on an elongate member capable of preventing overextension of an elongate member and/or a flexible member during use. For example, the first end of a safety wire can be attached to the proximal end of a shaft, the distal end of a shaft, between the proximal and distal ends of a shaft and on the exterior surface of the shaft, between the proximal and distal ends of a shaft and on the interior surface of the shaft, the proximal end of a flexible member, between the proximal and distal ends of a flexible member, and/or any other location considered suitable for a particular embodiment. Example locations considered suitable to attach the second end of a safety wire include the distal end of a cap, between the proximal and distal end of a cap and on the exterior surface of the cap, between the proximal and distal end of a cap and on the interior surface of the cap, the flexible member between the first end of the safety wire and the distal end of the flexible member, the distal end of the flexible member, and/or any other location considered suitable for a particular embodiment.

Any portion, or the entirety, of the length of elongate member 12 can be lined and/or coated with any suitable material to reduce the coefficient of friction between the outer surface of the elongate member and the surface in which the outer surface is intended to, or may, contact, or the surface defining a lumen or passageway of an elongate member and the surface of a device being passed through the lumen or passageway. Any suitable lining and/or coating capable of reducing the coefficient of friction is considered suitable, and skilled artisans will be able to select a suitable lining and/or coating according to a particular embodiment based on various considerations, such as the bodily passage within which the deflectable catheter is intended to be used. Example lubricious coatings considered suitable to reduce the coefficient of friction include, but are not limited to, polymers such as polyethylene (PE), polytetrafluoroethylene (PTFE), hydrophilic coatings that become lubricious upon wetting, and any other polymer or substance having properties that result in the lowering of the coefficient of friction between two surfaces.

Handle 14 can have any suitable structural configuration, can be formed of any suitable material, and can be fabricated using any suitable method of manufacture. Skilled artisans will be able to select a suitable structural configuration, material, and a method of manufacture for a handle according to a particular embodiment based on various considerations, including the devices intended to be housed by the handle. Example materials considered suitable to form a handle, or a component housed within a handle, include, but are not limited to, biocompatible materials, materials that can be made biocompatible, metals such as stainless steel, titanium, polymers, Pebax, nylon, polyethylene, polyurethane, silicone, and any other material considered suitable for a particular application. Example methods of manufacture considered suitable to fabricate a handle include extrusion processes, molding processes, and any other method considered suitable for a particular application.

In the illustrated embodiment, the handle 14 is attached to the proximal end 32 of the first shaft 28 and has a housing first portion 56, a housing second portion 58, an actuator housing 60, an actuator 62, and houses a control board 64. Handle 14 is similar to the handle described with respect to FIGS. 1, 2, 2A, 2B, 2C, 3, 4, and 5, described in U.S. Nonprovisional application Ser. No. 14/191,535, filed Feb. 27, 2014, and entitled Medical Devices, Systems, and Methods for the Visualization and Treatment of Bodily Passages. The entire contents of this application are hereby incorporated by reference into this disclosure. While a particular handle 14 has been illustrated as included in deflectable catheter 8, any suitable handle can be used, and skilled artisans will be able to select a suitable handle to use with a deflectable catheter according to a particular embodiment based on various considerations, including the treatment intended to be performed. Example alternative handles considered suitable to include with a deflectable catheter include any of the handles described in U.S. Nonprovisional application Ser. No. 14/191,535, filed Feb. 27, 2014, and entitled Medical Devices, Systems, and Methods for the Visualization and Treatment of Bodily Passages, and any other handle considered suitable for a particular embodiment.

Figure 8:
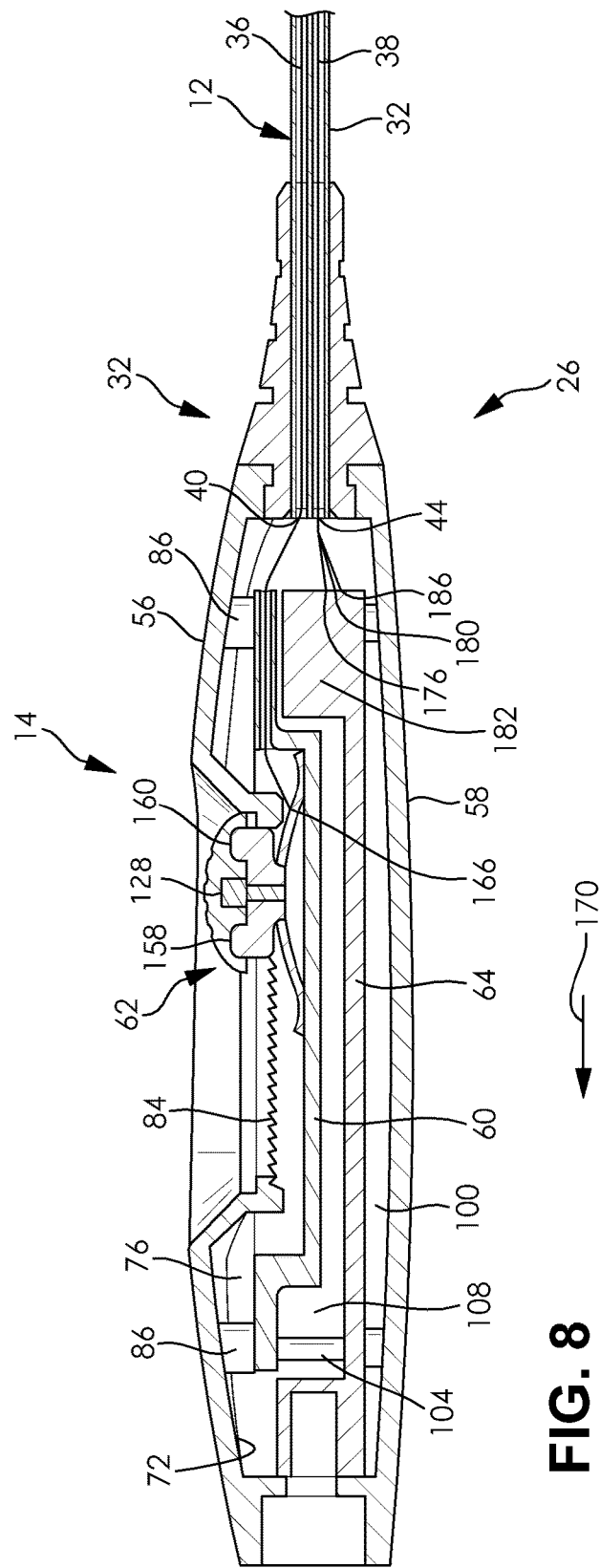
FIG. 8 is a partial sectional view of the deflectable catheter illustrated in FIG. 1, taken along the lengthwise axis of the deflectable catheter.
Figure 9:
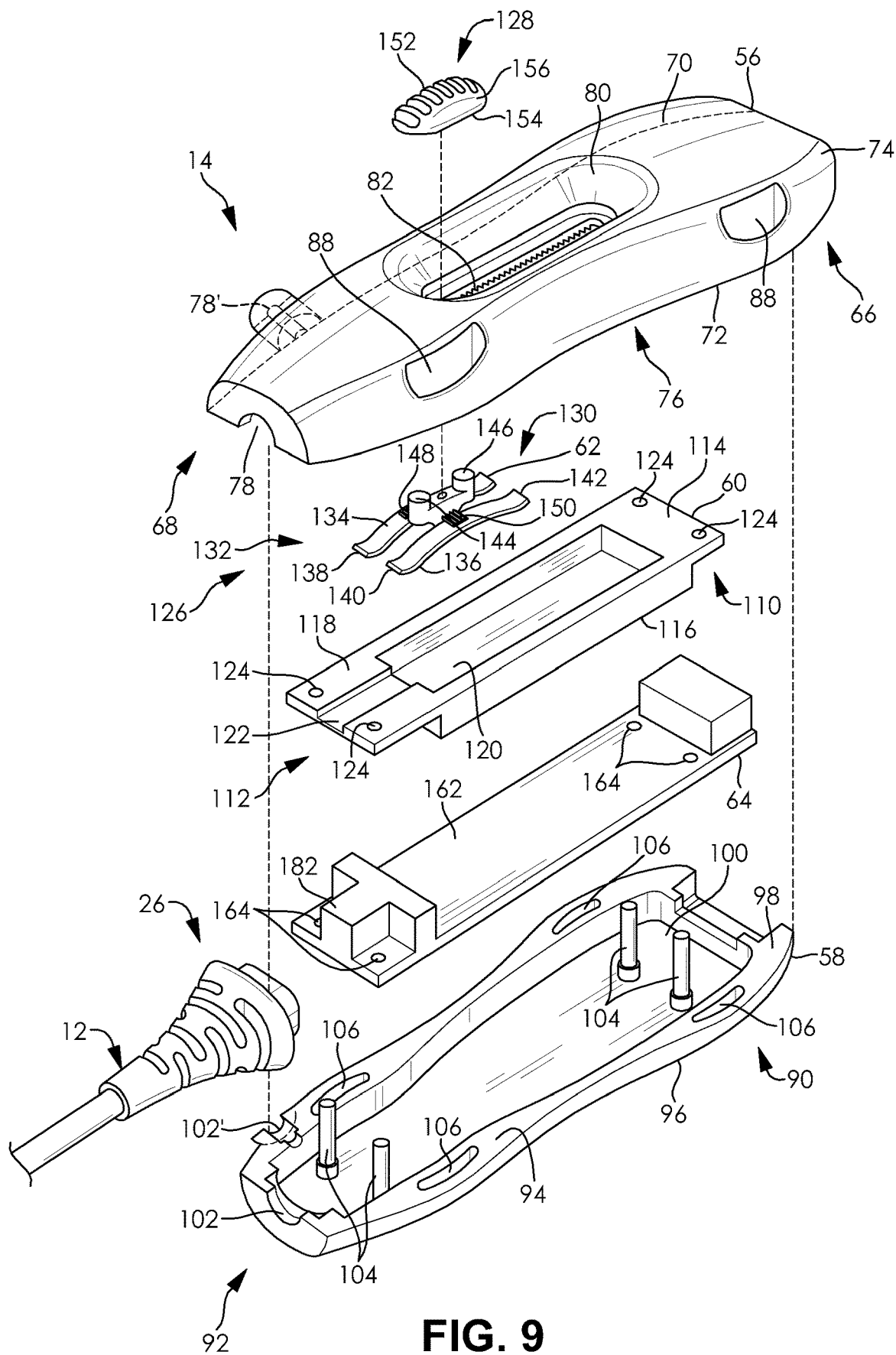
FIG. 9 is a partial exploded view of the deflectable catheter illustrated in FIG. 1.

The housing first portion 56 is adapted to be attached to the housing second portion 58. In the illustrated embodiment, as best shown in FIGS. 8 and 9, the housing first portion 56 has a proximal end 66, a distal end 68, a first side 70, a second side 72, and a body 74. The first side 70 of housing first portion 56 is opposably facing, or substantially opposably facing, the second side 72. The body 74 of housing first portion 56 defines a cavity 76, a first notch 78, a second notch 78', an actuator opening 80, a first toothed geometry 82, a second toothed geometry 84, a plurality of recesses 86, and a plurality of apertures 88.

The cavity 76 extends into the body 74 of housing first portion 56 from the second side 72 and is sized and configured to receive a portion of actuator housing 60, actuator 62, control board 64, data transfer cable 20, first optical fiber 22, second optical fiber 24, and/or irrigation tube 25. The first notch 78 extends into the body 74 from the second side 72 and extends from the distal end 68 to the cavity 76. The first notch 78 is sized and configured to receive a portion of elongate member 12. The second notch 78' extends into the body 74 from second side 72 and extends from a side of housing first portion 56 to the cavity 76. Second notch 78' is sized and configured to receive a portion of the irrigation tube 25. The actuator opening 80 is defined between the proximal end 66 and the distal end 68 of the housing first portion 56 and extends through the body 74 to provide access to the cavity 76. Each of the first toothed geometry 82 and second toothed geometry 84 extends into the cavity 76, is disposed along the length of the actuator opening 80, and is adapted to interact with a portion of actuator 62, as described in more detail herein. Alternative to each of the first toothed geometry 82 and second toothed geometry 84 extending along the length of the actuator opening 80, a first toothed geometry and/or a second toothed geometry of a housing first portion can extend along a portion of the length of an actuator opening. Each recess of the plurality of recesses 86 extends into the body 74 of the housing first portion 56 from the second side 72 and is sized and configured to receive a portion of a protuberance of the plurality of protuberances 104, as described in more detail below. Each aperture of the plurality of apertures 88 extends through the body 74 of the housing first portion 56 and is sized and configured to receive a portion of an attachment member (e.g., length of hook and loop fastener material) to attach the handle 14 to an individual or other device (e.g., patient, bed of patient, medical cart).

In the illustrated embodiment, as best shown in FIGS. 8 and 9, the housing second portion 58 has a proximal end 90, a distal end 92, a first side 94, a second side 96, and a body 98. The first side 94 of housing second portion 58 is opposably facing, or substantially opposably facing, housing the second side 96. The body 98 of housing second portion 58 defines a cavity 100, a first notch 102, a second notch 102', a plurality of protuberances 104, and a plurality of apertures 106.

The cavity 100 of housing second portion 58 extends into the body 98 from the first side 94 and is sized and configured to receive a portion of actuator housing 60, actuator 62, the control board 64, data transfer cable 20, first optical fiber 22, second optical fiber 24, and/or irrigation tube 25. The first notch 102 extends into the body 98 from the first side 94 and extends from the distal end 92 to the cavity 100. The first notch 102 is sized and configured to receive a portion of elongate member 12. The second notch 102' extends into the body 98 from the first side 94 and extends from a side of the housing second portion 58 to the cavity 100. The second notch 102' is sized and configured to receive a portion of the irrigation tube 25. The first notch 78' and second notch 102' cooperatively define a passageway 102", as shown in FIG. 1, which is sized and configured to receive a portion of the irrigation tube 25. Each protuberance of the plurality of protuberances 104 extends from the base of the cavity 100 and away from the second side 96. A portion of a protuberance of the plurality of protuberances 104 is sized and configured to be received by a recess of the plurality of recesses 86 to achieve attachment of the housing first portion 56 to the housing second portion 58. Each aperture of the plurality of apertures 106 extends through the body 98 of the housing second portion 58 and is sized and configured to receive a portion of an attachment member (e.g., length of hook and loop fastener material) to attach the handle 14 to an individual or other device (e.g., patient, bed of patient, medical cart).

As shown in FIG. 8, the cavity 76 of housing first portion 56 and the cavity 100 of housing second portion 58 cooperatively form a housing chamber 108 that is in communication with each of the first lumen 36 and second lumen 38 defined by the first shaft 28. The housing chamber 108 is sized and configured to house the actuator housing 60, a portion of actuator 62, the control board 64, a portion of data transfer cable 20, a portion of first optical fiber 22, a portion of second optical fiber 24, and/or a portion of irrigation tube 25. Thus, the handle 14 defines a chamber that is in communication with the lumens defined by the first shaft 28.

Optionally, the body 74 of the housing first portion 56 and/or the body 98 of the housing second portion 58 can define a notch, or opening, that extends through the body 74 and/or body 98 and into housing chamber 108. The notch and/or opening can be sized and configured to receive a portion of another device and allow the device (e.g., communications device, HDMI cable) to pass through notch and/or opening such that it can be attached to the control board 64.

While a plurality of recesses 86 and a plurality of protuberances 104 have been illustrated as accomplishing attachment between housing first portion 56 and housing second portion 58, any suitable structural arrangement and/or method of attachment is considered suitable between a housing first portion and a housing second portion. Skilled artisans will be able to select a suitable structural arrangement and/or method of attachment between a housing first portion and a housing second portion according to a particular embodiment based on various considerations, including the structural arrangement of an actuator. An example structural arrangement considered suitable includes forming a housing first portion and housing second portion as an integral component. Example structures for, and methods of, attachment between a housing first portion and a housing second portion considered suitable include using an adhesive, welding, fusing (e.g., heat fusing), threaded fasteners, snap fit configurations, and any other method of attachment considered suitable for a particular application.

While housing first portion 56 and housing second portion 58 have been illustrated as having a particular structural configuration, a housing can have any suitable structural configuration, and skilled artisans will be able to select a suitable structural configuration for a housing according to a particular embodiment based on various considerations, including the structural arrangement of a control board and/or actuator.

Actuator housing 60 has a proximal end 110, a distal end 112, a first side 114, a second side 116, and a body 118 that defines a recess 120, a notch 122, and a plurality of apertures 124. The first side 114 is opposably facing, or substantially opposably facing, the second side 116. The recess 120 extends into the body 118 from the first side 114 and is sized and configured to contain a portion of the actuator 62. The notch 122 extends into the body 118 from the first side 114 and extends from the distal end 112 to the recess 120. Each aperture of the plurality of apertures 124 extends through the body 118 and is sized and configured to receive a portion of a protuberance of the plurality of protuberances 104. While the actuator housing 60 has been illustrated as having a particular structural configuration, an actuator housing can have any suitable structural configuration, and skilled artisans will be able to select a suitable structural configuration for an actuator housing according to a particular embodiment based on various considerations, including the structural arrangement of a housing first portion and/or a housing second portion.

Actuator 62 comprises an actuator base 126 and an actuator control 128. Actuator base 126 comprises a proximal end 130, a distal end 132, a first side 134, a second side 136, a first base support 138, a second base support 140, and a body 142 that defines a first protuberance 144, second protuberance 146, first toothed geometry 148, and second toothed geometry 150. The first side 134 is opposably facing, or substantially opposably facing, the second side 136. Each of the first base support 138 and second base support 140 is biased such that it defines a curve between the proximal end 130 and the distal end 132 when no force is being applied to the actuator 62. Each of the first protuberance 144 and second protuberance 146 extends from the first side 134 and away from the second side 136. Each of the first toothed geometry 148 and second toothed geometry 150 extends from the first side 134 and away from the second side 136 and is complementary to first toothed geometry 82 and second toothed geometry 84 defined by the body 74 of the housing first portion 56. The first toothed geometry 82 and second toothed geometry 84 are sized and configured to interact with the first toothed geometry 148 and second toothed geometry 150 to provide releasable engagement between housing first portion 56 and actuator 62 when no force is being applied to the actuator 62.

The actuator control 128 has a first side 152, a second side 154, and a body 156 that defines a first recess 158, and second recess 160. The first side 152 is opposably facing, or substantially opposably facing, the second side 154. As shown in FIG. 8, each of the first recess 158 and second recess 160 extends into the body 156 of the actuator control 128 from the second side 154 and toward the first side 152. The first recess 158 is sized and configured to receive a portion of the first protuberance 144 of the actuator base 126 and the second recess 160 is sized and configured to receive a portion of the second protuberance 146 of the actuator base 126 such that the actuator control 128 is attached to the actuator base 126. While the actuator 62 has been illustrated as having a particular structural configuration, an actuator can have any suitable structural configuration, and skilled artisans will be able to select a suitable structural configuration for an actuator according to a particular embodiment based on various considerations, including the structural arrangement of a housing first portion and/or a housing second portion.

Control board 64 can comprise any suitable structure and include any suitable device, and skilled artisans will be able to select a suitable structure and device to include on a control board according to a particular embodiment based on various considerations, including the procedure intended to be performed. Example structures considered suitable include stripboards, printed circuit boards, and any other structure considered suitable for a particular application. Example devices considered suitable to include on a control board include energy storage devices, light sources, power sources, storage devices (e.g., computer-readable medium), data transfer devices, communication devices, high-definition multimedia interface (HDMI) compliant devices, HDMI ports, mobile high-definition link (MHL) compliant devices, MHL ports, energy transfer devices, processors, one or more switches for manipulating the function of, or data received from, any of the devices included on the control board, or attached to the control board, and any other device considered suitable for a particular application. For example, a control board can include computer readable media such that data obtained during the performance of a procedure can be transferred to another device during, or subsequent to, the performance of the procedure. In addition, or alternative to the embodiments described herein, a control board can be adapted to be attached to a power source or another device (e.g., computer, network) using a data transfer cable (e.g., HDMI cable, MHL cable), communications device, or communications cable, such that data obtained during the performance of a procedure can be transferred to another device during, or subsequent to, the performance of the procedure.

Control board 64 is adapted to obtain and process data and/or signals from imaging device 18 and store the data and/or signals on a local or remote storage device, communicate the data and/or signals to another device, and/or display the data and/or signals on a display device (e.g., monitor, television). The data and/or signals can be processed into any suitable format (e.g., S-video) and the functions of the imaging device 18, or the data received from imaging device 18, can be controlled, for example, using a graphical user interface (GUI) and an input device (e.g., mouse).

In the illustrated embodiment, control board 64 has a control board body 162 that defines a plurality of apertures 164. Each aperture of the plurality of apertures 164 extends through control board body 162 and is sized and configured to receive a portion of a protuberance of the plurality of protuberances 104 defined by housing second portion 58. In the illustrated embodiment, control board 64 is in signal communication with imaging device 18, first optical fiber 22, and second optical fiber 24, as described in more detail herein.

Optionally, one or more data transfer devices can be operatively attached to the control board 64 to transmit data to one or more devices. Skilled artisans will be able to select a suitable data transfer device to operatively attach to a control board to transfer data to one or more other devices according to a particular embodiment based on various considerations, including the type of data being transferred. Example data transfer devices considered suitable to operatively attach to a control board include data transmission cables, multi-conductor cables, coaxial cables, united serial bus (USB) cables, serial cables, Ethernet cables, HDMI cables, MHL cables, wireless transmission devices, and any other structure considered suitable for a particular application. Optionally, the distal end of the control board, or any other suitable portion of a control board, can comprise an HDMI port, or other suitable port or attachment mechanism, such that control board can be operatively attached to another device, such as a computer, network, storage device, computer readable storage medium, or any other suitable device, such as those described herein. Optionally, a handle can omit the inclusion of a control board and an imaging device, first optic fiber, and second optic fiber can be attached to a device separate from a deflectable catheter, as described in more detail herein.

The actuator 62 is moveable between an actuator first position, as shown in FIG. 1, and an actuator second position, not shown (e.g., actuator is disposed at the opposite end of the actuator opening 80, actuator is disposed at a position proximal to the actuator first position). Movement of actuator 62 between the actuator first position and actuator second position results in movement of elongate member 12 between the first, straight, configuration and the second, curved, configuration, as described in more detail herein.

As shown in FIG. 8, the actuator 62 is attached to wire member 16 and is adapted to be releasably fixed in the actuator first position and actuator second position via the interaction of first toothed geometry 82 with first toothed geometry 148 and second toothed geometry 84 with second toothed geometry 150. When a force is applied to actuator control 128 toward housing second portion 58, each of the first base support 138 and second base support 140 compresses against, or advances toward, the actuator housing 60 such that toothed geometries are not engaged with one another and the actuator 62 can be moved within actuator opening 80 between its first and second positions. Alternatively, when no force is applied to actuator control 128, each of the first base support 138 and second base support 140 compresses against and contacts the housing first portion 56 such that the toothed geometries defined by the housing first portion 56 and the actuator 62 are engaged with on another. Thus, the base supports 138, 140 have a first radius of curvature, or are straight, when a force is being applied to the actuator control 128 toward the housing second portion 58 and have a second radius of curvature when no force is being applied to the actuator control 128. The first radius of curvature is greater than the second radius of curvature. Engagement of the toothed geometries defined by the housing first portion 56 and the actuator 62 provides a mechanism to prevent, or substantially prevent, movement of elongate member 12, actuator 62, and/or wire member 16 when elongate member 12 is in the straight configuration or defines a desired radius of curvature. For example, including a mechanism for releasably fixing actuator 62 along the length of actuator opening 80 allows the configuration of elongate member 12 to be releasably fixed, or substantially fixed, when a procedure is being performed.

While an actuator that is moveable along the length of a housing (e.g., linear actuator) is illustrated, any suitable actuator can be used to move an elongate member between a first configuration and second configuration, and skilled artisans will be able to select a suitable actuator to include on a deflectable catheter according to a particular embodiment based on various considerations, including the radius of curvature intended to be defined by an elongate member when the actuator is moved between an actuator first position and an actuator second position. Example actuators considered suitable include linear actuators, rotatable actuators, pivotable actuators, electro-mechanical actuators, and any other actuator considered suitable for a particular application.

While housing first portion 56 has been illustrated as having first toothed geometry 82 and second toothed geometry 84 and actuator base 126 has been illustrated as having first toothed geometry 148 and second toothed geometry 150, any suitable structural configuration capable of maintaining the position of an actuator in an actuator first position and/or actuator second position, or a position between the actuator first position and the actuator second position, can be used. Skilled artisans will be able to select a suitable structural configuration to maintain the position of an actuator according to a particular embodiment based on various considerations, including the structural arrangement of an elongate member. Example structural arrangements considered suitable include, but are not limited to, snap-fit configurations, press-fit configurations, and any other structural configuration considered suitable for a particular application.

Wire member 16 can have any suitable outside diameter and length, and skilled artisans will be able to select a suitable outside diameter and length for a wire member according to a particular embodiment based on various considerations, including the desired bodily passage within which a deflectable catheter is intended to be used. For example, wire members that have an outside diameter between about 0.003 inches and about 0.015 inches or between about 0.008 inches and about 0.010 inches are considered suitable.

Wire member 16 can be formed of any suitable material, and skilled artisans will be able to select a suitable material to form a wire member according to a particular embodiment based on various considerations, including the material that forms an elongate member. Example materials considered suitable to form a wire member include biocompatible materials, materials that can be made biocompatible, braided materials, polymers, nylon, metals such as stainless steel, titanium, and nickel-titanium alloy (e.g., Nitinol), and any other material considered suitable for a particular application. Any portion, or the entirety, of the length of wire member 16 can be lined and/or coated with any suitable material to reduce the coefficient of friction between the outer surface of the wire member 16 and the surface in which the outer surface is intended to, or may, contact. Any suitable lining and/or coating capable of reducing the coefficient of friction is considered suitable, and skilled artisans will be able to select a suitable lining and/or coating according to a particular embodiment based on various considerations, such as the materials that form an elongate member. Example lubricious coatings considered suitable to reduce the coefficient of friction between a wire member and the surface in which the outer surface is intended to, or may, contact include polymers such as polyethylene (PE), polytetrafluoroethylene (PTFE), hydrophilic coatings that become lubricious upon wetting, and any other polymer or substance having properties that result in the lowering of the coefficient of friction between two surfaces. For example, a portion, or the entirety, of the length of wire member 16 can be lined and/or coated with a material to reduce the coefficient of friction between the wire member 16 and the elongate member 12 when moving the elongate member 12 between a curved configuration and a straight, or substantially straight, configuration relative to embodiments that do not include a lining and/or coating.

Figure 4:
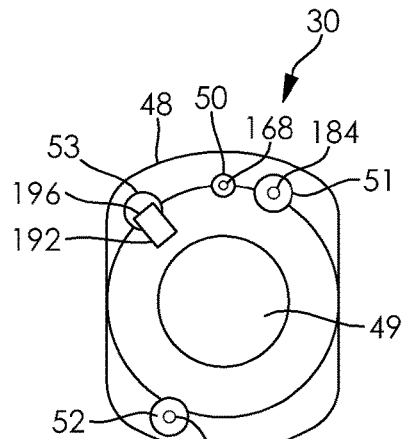
FIG. 4 is an end view of the distal end of the deflectable catheter illustrated in FIG. 1.
Figure 5:
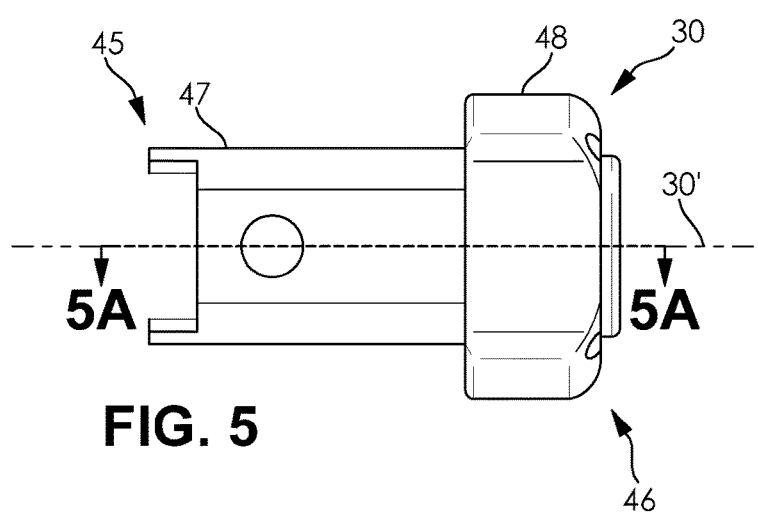
FIG. 5 is a side view of the cap of the deflectable catheter illustrated in FIG. 1 free of the deflectable catheter.
Figure 6:
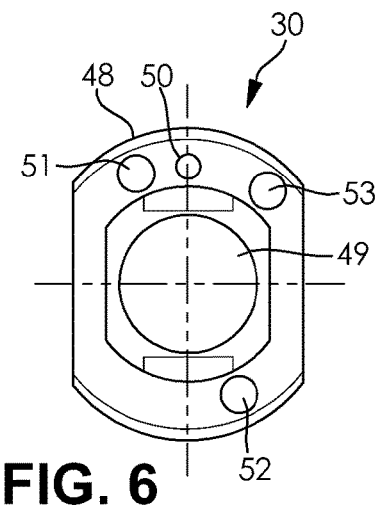
FIG. 6 is an end view of the proximal end of the cap of the deflectable catheter illustrated in FIG. 1 free of the deflectable catheter.
Figure 5A:
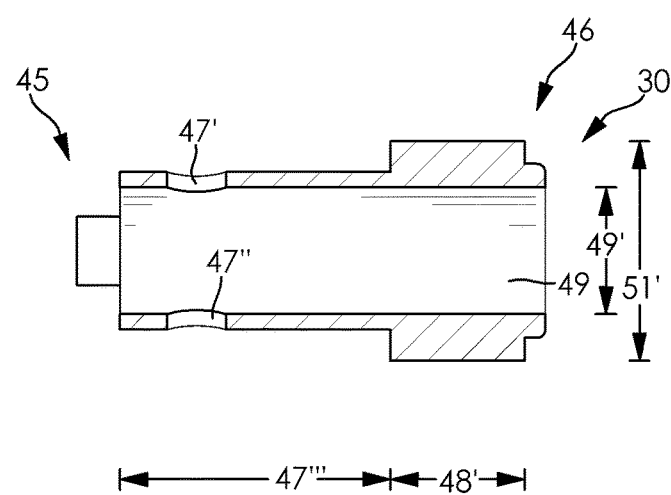
FIG. 5A is a sectional view of the cap illustrated in FIG. 5, taken along line 5A-5A.

In the illustrated embodiment, the wire member 16 comprises a wire member first end 166, as shown in FIG. 8, and a wire member second end 168, as shown in FIG. 4. The wire member first end 166 can be attached to any suitable portion of the actuator 62. In the illustrated embodiment, the wire member first end 166 is attached to the first protuberance 144 of the actuator base 126. The wire member 16 extends from the wire member first end 166 through the first lumen 36 defined by the first shaft 28, through the passageway 44 defined by the first flexible member 29, and is attached to the cap 30 within the wire member opening 50 (e.g., using an adhesive, welding). As shown in FIG. 2, the wire member 16 is disposed between the first flexible member 29 and the exterior surface of the cap 30 from the flange 48 to the proximal end 45 of the cap 30.

In the illustrated embodiment, each of the distal end of the first lumen 36 and the wire member second end 168 is disposed on a plane that extends from the lengthwise axis 11 of the deflectable catheter 8 when the elongate member 12 is in the straight configuration. Thus, the distal end of the first lumen 36 and the wire member second end 168 are spaced longitudinally along the length of elongate member 12 and are disposed linearly along elongate member 12 when the elongate member 12 is in the straight configuration. This configuration provides a mechanism for moving the elongate member 12 between a straight configuration and a curved configuration such that the distal end of the first lumen 36 and the wire member second end 168 are disposed in the same plane during movement between the straight configuration and the curved configuration. However, alternative embodiments can include an elongate member that has a wire member second end that is not disposed on the same plane as the distal end of the first lumen and the lengthwise axis of the elongate member when the elongate member is moved between the straight and curved configurations.

While the distal end of the first lumen 36 and the wire member second end 168 are illustrated as disposed linearly along elongate member 12 and on a plane that extends from the elongate member lengthwise axis 11, the distal end of a lumen defined by a shaft and a wire member second end can be positioned at any suitable location relative to one another on an elongate member. Skilled artisans will be able to select a suitable position to locate the distal end of a lumen defined by a shaft relative to a wire member second end of an elongate member according to a particular embodiment based on various considerations, including the structural arrangement of the bodily passage within which a deflectable catheter is intended to be used. Example locations considered suitable to position the distal end of a lumen defined by a shaft relative to a wire member second end of an elongate member include positioning the distal end of the lumen and the wire member second end such that they are contained on a plane that extends from the elongate member lengthwise axis, positioning the distal end of the lumen such it is disposed on a first plane that extends from the elongate member lengthwise axis and positioning the wire member second end such that it is disposed on a second plane that extends from the elongate member lengthwise axis, the first plane is different than the second plane and is disposed at an angle to the second plane. Example angles considered suitable between a first plane that contains the distal end of a lumen and a second plane that contains a wire member second end include an angle equal to about 45 degrees, an angle between about 1 degree and about 90 degrees, an angle about 90 degrees, an angle between about 90 degrees and about 180 degrees, an angle between about 180 degrees and about 270 degrees, an angle between about 270 degrees and about 360 degrees, and any other angle considered suitable for a particular application. Thus, the distal end of a lumen defined by a shaft and a wire member second end can be disposed linearly or offset from one another about the circumference of an elongate member relative to the lengthwise axis of the elongate member.

A wire member can be attached to an actuator (e.g., first protuberance 144) using any suitable structure for, or method of, attachment between two components, and skilled artisans will be able to select a suitable structure for, or method of, attachment between a wire member and an actuator according to a particular embodiment based on various considerations, including the material that forms the wire member and/or actuator. Example structures for, and methods of, attachment between a wire member and an actuator considered suitable include, but are not limited to, bonding a wire member and an actuator to one another, using an adhesive, fusing, welding, tying a wire member to an actuator, passing a wire member through an aperture defined by an actuator (e.g., actuator protuberance) and tying the wire member about the actuator, passing a wire member through an aperture defined by an actuator (e.g., actuator protuberance) and attaching a stopper having an outside diameter greater than the aperture defined by the actuator to the wire member, using a set screw that passes through a threaded passageway defined by a portion of an actuator that can be tightened on a wire member to achieve attachment, and any other structure for, or method of, attachment between two components considered suitable for a particular application.

While the wire member second end 168 is illustrated as attached to the cap 30 within the wire member opening 50, a wire member second end can be attached at any suitable location along the length of a cap, elongate member, shaft, and/or flexible member using any suitable structure for, or method of, attachment between two components. Skilled artisans will be able to select a suitable location to attach a wire member second end to an elongate member and a suitable structure for, or method of, attachment between a wire member and an elongate member according to a particular embodiment based on various considerations, including the axial length of the elongate member and/or the radius of curvature desired to be achieved by the elongate member when in a second configuration. Example structures for, and methods of, attachment between a wire member and a cap, or any other portion of a deflectable catheter, considered suitable include using an adhesive, welding, fusing (e.g., heat fusing), and any other structure for, or method of, attachment between two components considered suitable for a particular application.

In use, movement of actuator 62 away from elongate member distal end 28, as shown by arrow 170 in FIG. 8, from the actuator first position, as shown in FIG. 1, to the actuator second position (not shown) causes wire member 16 to move in a proximal direction such that wire member first end 166 advances away from the proximal end 26 of the elongate member 12. This creates tension in the wire member 16 that results in movement of wire member second end 168 and elongate member 12 such that the elongate member 12 moves from a straight configuration, as shown in FIG. 1, to a curved configuration, as shown in FIG. 7, in which elongate member 12 defines a curve 172 at a radius of curvature 174. Movement of actuator 62 toward elongate member distal end 28, in a direction opposite that of arrow 170, reduces, or eliminates, tension in wire member 16 and results in elongate member 12 returning to the straight configuration. Thus, when actuator 62 is in the actuator first position, elongate member 12 is in the straight configuration and when actuator 62 is in the actuator second position, elongate member 12 is in the curved configuration.

When elongate member 12 is in the curved configuration, the portion of elongate member 12 disposed distal to curve 172 is disposed at an angle to the portion of the elongate member 12 disposed proximal to curve 172 relative to an axis that is parallel to the lengthwise axis 11 of the deflectable catheter 8. The portion of an elongate member disposed distal to a curve can be disposed at any suitable angle to the portion of the elongate member disposed proximal to the curve, and skilled artisans will be able to select a suitable angle according to a particular embodiment based on various considerations, including the desired procedure intended to be performed. Example angles considered suitable to define between a portion of an elongate member disposed distal to a curve and a portion of an elongate member disposed proximal to the curve include angles between about 0 degrees and 180 degrees, about 45 degrees, about 90 degrees, about 120 degrees, and any other angle considered suitable for a particular application.

The radius of curvature 174 defined by elongate member 12 can vary and be based upon at least the material(s) that form the elongate member 12, the location of the actuator second position, the length of elongate member 12, the length of wire member 16, the axial length of actuator opening 80 as it relates to the length of elongate member 12, and/or the distance between the distal end 34 of the first shaft 28 and the distal end 42 of the first flexible member 29. For example, if a small radius of curvature 174 is desired, the length of wire member 16 can be reduced as it relates to the length of elongate member 12 and/or the length of actuator opening 80 can be increased as it relates to the length of elongate member 12. Alternatively, if a large radius of curvature 174 is desired, the length of wire member 16 can be increased as it relates to the length of elongate member 12 and/or the length of actuator opening 80 can be decreased as it relates to the length of elongate member 12. Alternatively, adjustment of actuator 62 provides a mechanism for manipulating the radius of curvature 174 defined by elongate member 12 such that a desired radius of curvature can be achieved. Residual tension in wire member 16 can be eliminated, or substantially eliminated, when actuator 62 is in the actuator first position (e.g., actuator 62 is near, or at, the distal end of actuator opening 80) to configure the elongate member 12 such that it is straight, or substantially straight, along its length when the actuator 62 is in the actuator first position. Optionally, an elongate member can be formed such that one or more curves are predefined between an elongate member proximal end and an elongate member distal end.

In the illustrated embodiment, the wire member 16 has a length that is greater than the sum of the length 35 of the first shaft 28 and the length 43 of the first flexible member 29. However, alternative embodiments can include a wire member 16 that has any suitable length. Example lengths considered suitable for a wire member include lengths that are greater than, less than, or equal to, the length of an elongate member, the length of a shaft, and/or the length of a flexible member.

Movement of an elongate member 12 between a straight configuration and a curved configuration allows the deflectable catheter 8 to be advanced through tortuous bodily passages, such as airways, sinus cavities, and/or sinus passages and to position the distal end 27 of the elongate member 12. In addition, movement between a straight and curved configuration allows for the elongate member 12 to be manipulated such that distal end 27 of the elongate member 12 can be positioned in various configurations to view various aspects of a bodily passage (e.g., during the performance of a sleep study).

The imaging device 18 is disposed within the passageway 49 defined by the cap 30, is attached within the passageway 49 defined by the cap 30, and is operatively coupled to the control board 64 by the data transfer cable 20. Imaging device 18 is adapted to obtain images of features and/or material disposed distal to elongate member 12 and transmit the images to the control board 64 via data transfer cable 20, or to another device wirelessly, or otherwise. Alternative to the imaging device 18 being disposed at the distal end 27 of the elongate member 12, an imaging device can be disposed between an elongate member proximal end and an elongate member distal end such that the imaging device is disposed through an opening defined by the body of the elongate member and can obtain images radially from the elongate member. Optionally, an objective or image-forming lens can be disposed distal to imaging device 18 that is adapted to focus an image upon the imaging device 18.

Imaging device 18 can comprise any suitable device and/or structure capable of obtaining one or more images and transmitting the image to another device. Any suitable imaging device can be used in a deflectable catheter, and skilled artisans will be able to select a suitable imaging device to include with a deflectable catheter according to a particular embodiment based on various considerations, including the bodily passage in which the deflectable catheter is intended to be used. Example imaging devices considered suitable include self-scanning solid state imaging devices, charge coupled (CCD) sensors, complementary metal-oxide semi-conductor (CMOS) sensors, and any other imaging device considered suitable for a particular application. An example imaging device considered suitable includes the imaging device included on the eyeMAX (eyeMAX is a registered trademark of Richard Wolf GmbH Corporation of Knittlingen, Federal Republic of Germany) endoscope with chip on-the-tip, or chip-in-tip, technology.

The data transmitted by imaging device 18 can comprise any suitable form of data, and skilled artisans will be able to select a suitable form of data to transmit from an imaging device according to a particular embodiment based on various considerations, including the type of imaging device being used with a deflectable catheter. Example forms of data considered suitable include, but are not limited to, analog data, RGB data, RGB data that is digitized and then amplified, digital data, and any other data considered suitable for a particular application.

The data transfer cable 20 has a first end 176 operatively attached to control board 64, as shown in FIG. 8, and a second end 178 operatively attached to imaging device 18, as shown in FIG. 2. The data transfer cable 20 can comprise any suitable structure capable of transmitting data and/or power from one location to another, and skilled artisans will be able to select a suitable structure to transmit data and/or power according to a particular embodiment based on various considerations, including the structural arrangement of an elongate member. Alternatively, the data transfer cable 20 can be omitted and imaging device 18 can be operatively connected to a wireless data transmission device, located at any suitable location on a deflectable catheter 8 (e.g., cap 30, control board 64), such that the images obtained by the imaging device 18 can be wirelessly transmitted to a control board or other device. Alternatively, the imaging device 18 can be directly attached to a display, or other device, using the data transfer cable 20 to provide still and/or live footage to the display for review by a user. Alternatively, multiple imaging devices can be used in conjunction with, or separate from, one another.

The first optical fiber 22 has a first end 180 operatively attached to a light source 182 included on the control board 64, as shown in FIG. 8, and a second end 184 disposed within the first optical fiber opening 51 defined by the cap 30, as shown in FIG. 4. The first optical fiber 22 is attached to the cap 30 within the first optical fiber opening 51. The second optical fiber 24 has a first end 186 operatively attached to the light source 182 included on the control board 64, as shown in FIG. 8, and a second end 188 disposed within the second optical fiber opening 52 defined by the cap 30, as shown in FIG. 4. The second optical fiber 24 is attached to the cap 30 within the second optical fiber opening 52. Each of the first optical fiber 22 and the second optical fiber 24 defines a light path along its length. Light generated by the light source 182 travels through the light path defined by first optical fiber 22 and second optical fiber 24 and is emitted axially from each optical fiber second end 184, 188. Each of the first optical fiber 22 and the second optical fiber 24 can be attached to the cap 30 using any suitable structure for, or method of, attachment between two components. Example structures for, and methods of, attachment between an optical fiber and a cap considered suitable include using an adhesive, welding, fusing (e.g., heat fusing), using threaded connections, and any other structure or method of attachment considered suitable for a particular embodiment.

Any suitable optical fiber can be used in combination with deflectable catheter, and skilled artisans will be able to select a suitable optical fiber to include on a deflectable catheter according to a particular embodiment based on various considerations, including the desired bodily passage within which the deflectable catheter is intended to be disposed. Example optical fibers considered suitable include, but are not limited to, commercially available optical fibers such as plastic optical fibers and glass optical fibers, with or without cladding.

Any suitable light source can be included on a control board of a deflectable catheter, and skilled artisans will be able to select a suitable light source to include on a control board according to a particular embodiment based on various considerations, including the type of treatment intended to be performed. Example light sources considered suitable include, but are not limited to, commercially-available light sources such as xenon, laser, LED, and halogen light sources. Alternatively, the first end of an optical fiber can be attached to a light source that is separate from a control board. Optionally, the light source can include a fiber coupling (not shown) which provides communication between a light source and a first optical fiber and a second optical fiber.

It is noted that while a first optical fiber 22 and a second optical fiber 24 have been illustrated, one or more different optical fibers can be used in combination, or independently, to provide axially directed and/or radially directed light. The one or more optical fibers can extend through the same or different lumens of an elongate member and can be operatively connected or attached to the same or two different light sources.

The irrigation tube 25 comprises an elongate tubular member that has a first end 190, as shown in FIG. 1, a second end 192, as shown in FIG. 4, and defines a lumen 194 and a bend 196. The lumen 194, as shown in FIG. 2, extends from the first end 190 to the second send 192 of the irrigation tube 25. The first end 190 is disposed within the passageway 102″ cooperatively defined by the second notch 78′ defined by the housing first portion 56 and the second notch 102′ defined by the housing second portion 58. The irrigation tube 25 can have any suitable outside diameter, length, and be formed of any suitable material. Example outside diameters considered suitable for a irrigation tube include outside diameters that are less than the inside diameter of the second lumen defined by a shaft, diameters that are less than the inside diameter of the passageway cooperatively defined by first and second housing portions, and any other diameter considered suitable for a particular embodiment. Example lengths considered suitable for an irrigation tube include lengths that are greater than the length of the elongate member, lengths that are greater than a shaft, lengths that are greater than a flexible member, and any other length considered suitable for a particular embodiment. Example materials considered suitable to form an irrigation tube include biocompatible materials, materials that can be made biocompatible, metals such as stainless steel, titanium, nickel-titanium alloy (e.g., Nitinol), polymers, Pebax, nylon, polyethylene, polyurethane, silicone, coiled materials, braided materials, and any other material considered suitable for a particular application.

The first end 190 of the irrigation tube 25 is disposed outside of the passageway 190 cooperatively defined by the housing first portion 56 and the housing second portion 58 and can include any suitable connector and/or adapter capable of attaching one or more devices to the irrigation tube 25. Skilled artisans will be able to select a suitable connector and/or adapter to include on the first end of an irrigation tube according to a particular embodiment based on various considerations, including the materials that form the irrigation tube. Example connectors and/or adapters considered suitable to include on an irrigation tube include threaded connectors, Tuohy Borst adapters, luer lock connectors, and any other connector and/or adapter considered suitable for a particular embodiment.

As shown in FIG. 4, the irrigation tube 25 is disposed within, and attached to, the irrigation opening 53 defined by the cap 30. The irrigation tube 25 defines the bend 196 between the first end 190 and second end 192 of the irrigation tube 25 such that the second end 192 of the irrigation tube 25 can be oriented in any manner considered suitable for a particular embodiment. For example, in the illustrated embodiment, the second end 192 of the irrigation tube 25 is directed toward the distal end of the imaging device 18 (e.g., toward the lengthwise axis of the elongate member) such that irrigation fluid can be passed through the lumen 194 defined by the irrigation tube 25 and the imaging device 18 can be cleaned during the performance of a procedure. The irrigation tube 25 can be attached to the cap 30 using any suitable structure for, or method of, attachment between two components. Example structures for, and methods of, attachment between an irrigation tube and a cap considered suitable include using an adhesive, welding, fusing (e.g., heat fusing), using threaded connections, and any other structure or method of attachment considered suitable for a particular embodiment.

Alternative to defining a bend, an irrigation tube can define an aperture at, or near, the second end of the irrigation tube that is directed toward the imaging device (e.g., aperture is defined at an angle relative to the lengthwise axis of the irrigation tube). Alternative to defining a bend, a stainless steel tubular member can be disposed within the distal opening of an irrigation tube. In these alternative embodiments, the irrigation tube can be formed of a polymer, or other suitable material, and the stainless steel tubular member can define a bend between its proximal and distal ends such that when the irrigation tube is attached within the cap, the distal end of the stainless steel tubular member is directed toward an imaging device and/or the lengthwise axis of the deflectable catheter.

In the embodiment illustrated, each of the wire member 16, first optical fiber 22, second optical fiber 24, and irrigation tube 25 is disposed between the interior surface of the first flexible member 29 and the exterior surface of the shaft 47 of the cap 30 from the proximal end 45 of the cap 30 to the flange 48. Alternatively, a tubular member can be attached to the shaft of a cap such that the exterior surface of the tubular member is attached to a first flexible member and each of the wire member, first optical fiber, second optical fiber, and irrigation tube is disposed within the tubular member, disposed between the interior surface of the tubular member and the shaft of the cap, and extend to an opening defined by the flange of the cap, as described herein. Alternatively, a dual lumen shaft can be attached to the shaft of a cap such that the exterior surface of the dual lumen shaft is attached to a first flexible member and the wire member is disposed in a first lumen defined by the dual lumen shaft and each of the first optical fiber, second optical fiber, and irrigation tube is disposed in a second lumen defined by the dual lumen shaft. The dual lumen shaft can be attached to the cap such that the lumen within which the wire member is disposed is coaxial with the wire member opening defined by the cap. Each of the first optical fiber, second optical fiber, and irrigation tube extends through the second lumen defined by the dual lumen shaft and is disposed between the interior surface of the second lumen defined by the dual lumen shaft and the exterior surface of the shaft of the cap, and extend to an opening defined by the flange of the cap, as described herein.

While a portion of the wire member 16 has been illustrated as being disposed within the first lumen 36 defined by the first shaft 28 and a portion of each of the imaging device 18, data transfer cable 20, first optical fiber 22, second optical fiber 24, and irrigation tube 25 has been illustrated as being disposed within the second lumen 38 defined by the first shaft 28, other configurations are considered suitable. For example, a portion of a wire member can be positioned within the second lumen defined by a shaft and/or a portion of an imaging device, data transfer cable, first optical fiber, second optical fiber, and/or irrigation tube can be positioned in the first lumen defined by a shaft. Alternatively, depending on the structural arrangement of a shaft, the components can be disposed within a lumen defined by a shaft independent of any other component (e.g., shaft defines a lumen for each component) or each component can be disposed within the same lumen defined by a shaft (e.g., shaft defines a single lumen). Optionally, an imaging device, data transfer cable, first optical fiber, second optical fiber, and/or irrigation tube can be omitted from a deflectable catheter.

FIGS. 10, 11, 12, 13, 14, 15, and 16, illustrate another deflectable catheter 208. The deflectable catheter 208 is similar to the deflectable catheter 8 illustrated in FIGS. 1, 2, 3, 4, 5, 5A, 6, 7, 8, and 9, and described above, except as detailed below. Reference numbers in FIGS. 10, 11, 12, 13, 14, 15, and 16 refer to the same structural element or feature referenced by the same number in FIGS. 1, 2, 3, 4, 5, 5A, 6, 7, 8, and 9, offset by 200. Thus, the deflectable catheter 208 includes an elongate member 212, a handle 214, a wire member 216, an imaging device 218, a data transfer cable 220, a first optical fiber 222, a second optical fiber 224, and an irrigation tube 225. The imaging device 218, data transfer cable 220, first optical fiber 222, second optical fiber 224, and irrigation tube 225 have been omitted from FIGS. 10, 11, 15, and 16 for clarity.

Figure 10:
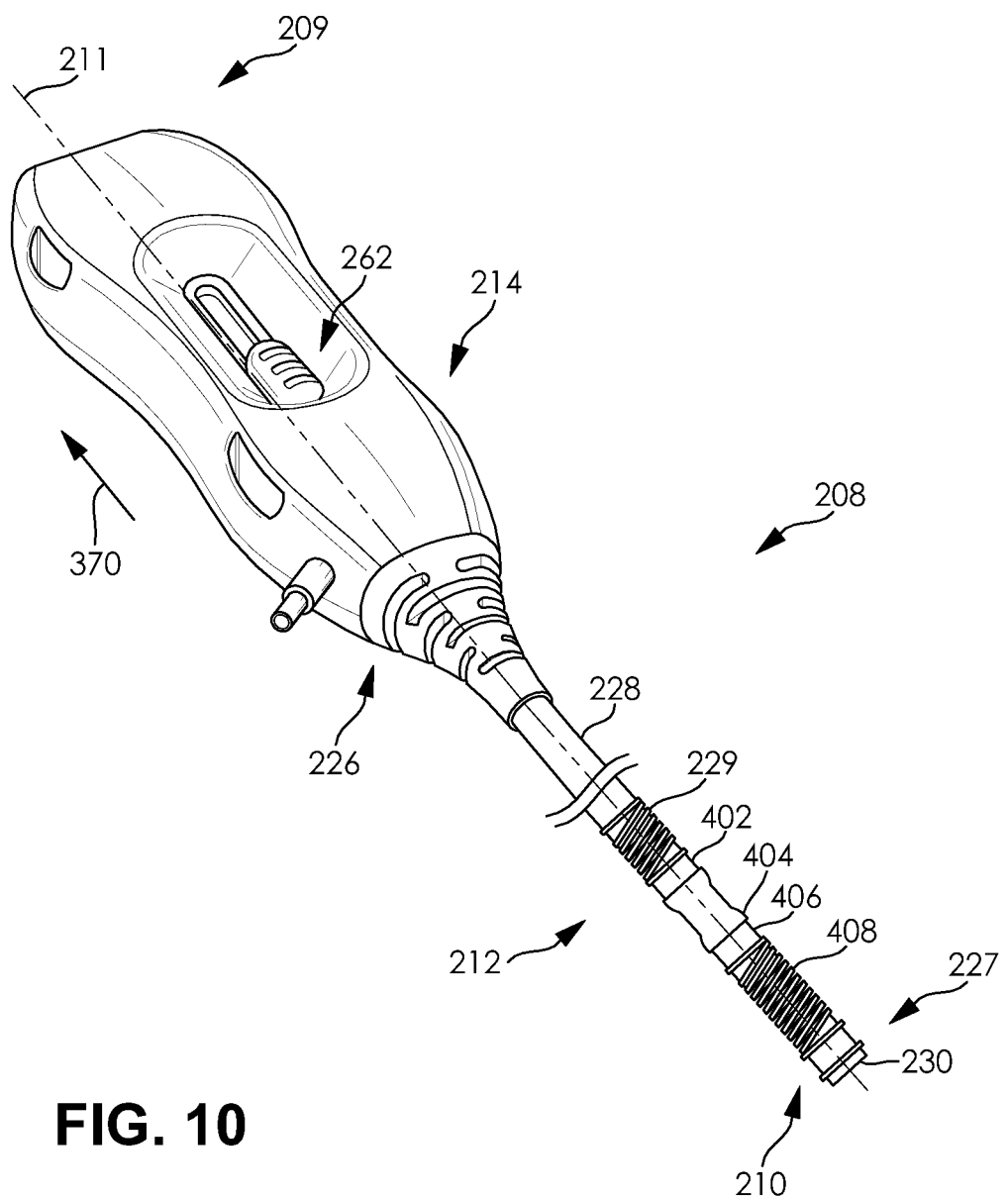
FIG. 10 is a perspective view of another deflectable catheter in a first configuration.

In the illustrated embodiment, the elongate member 212 has a proximal end 226, a distal end 227, a first shaft 228, a first flexible member 229, a second shaft 402, a tubular member 404, a third shaft 406, a second flexible member 408, a safety wire 410, and a cap 230. The safety wire 410 has only been illustrated in FIGS. 13, 14, and 15 for clarity. The elongate member 212 has a first, straight, configuration, as shown in FIG. 10, and a second, curved, configuration, as shown in FIG. 16.

Elongate member 208 can have any suitable outside diameter and any suitable length, and skilled artisans will be able to select a suitable outside diameter and length for an elongate member according to a particular embodiment based on various considerations, including the desired bodily passage within which a deflectable catheter is intended to be used. Example lengths considered suitable for an elongate member include lengths between 60 centimeters and 150 centimeters, lengths between about 60 centimeters and 150 centimeters, and any other length considered suitable for a particular embodiment. Example outside diameters considered suitable for an elongate member include outside diameters between 1.0 millimeter and 8.0 millimeters, between about 1.0 millimeter and about 8.0 millimeters, between 2.0 millimeters and 6.0 millimeters, between about 2.0 millimeters and about 6.0 millimeters, between 3.0 millimeters and 5.0 millimeters, between about 3.0 millimeters and about 5.0 millimeters, equal to, substantially equal to, or about 4.0 millimeters, outside diameters less than, or equal to, 4.0 millimeters, and any other outside diameter considered suitable for a particular embodiment.

The second shaft 402 has a proximal end 412, a distal end 414, and a body that defines a first lumen 416 and a second lumen 418. Each of the first lumen 416 and the second lumen 418 extends from the proximal end 412 of the second shaft 402 to the distal end 414 of the second shaft 402. The first lumen 416 has a diameter that is less than the diameter of the second lumen 418. The first lumen 416 is sized and configured to receive a portion of the wire member 216 and a portion of the safety wire 410. The second lumen 418 is sized and configured to receive a portion of the imaging device 218, data transfer cable 220, first optical fiber 222, second optical fiber 224, and/or irrigation tube 225. In the embodiment illustrated, the first lumen 236 defined by the first shaft 228 is disposed on a first shaft lengthwise axis and the first lumen 416 defined by the second shaft 402 is disposed on a second shaft lengthwise axis. The first shaft lengthwise axis and second shaft lengthwise axis are coaxial and parallel to the lengthwise axis 211 of the deflectable catheter 208. However, the first lumen defined by a first shaft can be disposed on a first axis that is disposed on a first plane that contains the lengthwise axis of the deflectable catheter and the first lumen defined by a second shaft can be disposed on a second axis that is disposed on a second plane that contains the lengthwise axis of the deflectable catheter. The first plane can be disposed at an angle to the second plane relative to the lengthwise axis of the deflectable catheter. Example angles considered suitable between a first plane and a second plane include angles equal to about 45 degrees, angles between about 1 degree and about 90 degrees, angles about 90 degrees, angles between about 90 degrees and about 180 degrees, angles between about 180 degrees and about 270 degrees, angles between about 270 degrees and about 360 degrees, angles less than, great than, or equal to 45 degrees, and any other angle considered suitable for a particular application. Thus, the first lumen defined by a first shaft can be coaxial or offset from the first lumen defined by a second shaft.

In the embodiment illustrated, the second shaft 402 is attached to the distal end of the first flexible member 229 such that a portion of the second shaft 402 is disposed within the passageway 244 defined by the first flexible member 229. The first flexible member 229 is attached to the second shaft 402 using an adhesive. Alternatively, a second shaft can be attached to the distal end of a first flexible member, or embedded within the material that forms the first flexible member. The distal end 234 of the first shaft 228 is disposed from the proximal end 412 of the second shaft 402 a distance 403 as measured when the deflectable catheter 208 is in the straight configuration. In the embodiment illustrated, the distance 403 is equal to 3.0 millimeters.

While the distal end 234 of the first shaft 228 has been illustrated as disposed from the proximal end 412 of the second shaft 402 a distance 403, the distal end of a first shaft can be disposed any suitable distance from the proximal end of a second shaft when a deflectable catheter is in the straight configuration. Skilled artisans will be able to select a suitable distance between the distal end of a first shaft and the proximal end of a second shaft according to a particular embodiment based on various considerations, including the degree of curvature intended to be accomplished when a deflectable catheter is in the second configuration. Example distances considered suitable between the distal end of a first shaft and the proximal end of a second shaft include distances equal to 3.0 millimeters, equal to about 3.0 millimeters, equal to between 1.0 millimeter and 4.0 millimeters, equal to between about 1.0 millimeter and about 4.0 millimeters, and any other distance considered suitable for a particular embodiment. For example, a first embodiment of a deflectable catheter can have a first distance disposed between the distal end of a first shaft and the proximal end of a second shaft and a second embodiment of a deflectable catheter can have a second distance disposed between the distal end of a first shaft and the proximal end of a second shaft that is less than the first distance. The first embodiment can define a radius of curvature in the second configuration that is less than a radius of curvature that the second embodiment can define when it is in the second configuration. Thus, by increasing the distance between the distal end of a shaft and the proximal end of another shaft, the radius of curvature can be decreased.

The first flexible member 229 has a length 243 that is greater than the distance 403 between the distal end 234 of the first shaft 228 and the proximal end 412 of the second shaft 402. In the embodiment illustrated, the first flexible member 229 has a length 243 that is equal to 1.0 centimeter. However, alternative embodiments can include a first flexible member that has a length that is less than, equal to, or substantially equal to, the distance between the distal end of a first shaft and the proximal end of a second shaft. While the first flexible member 229 has been illustrated as having a particular length 243, a flexible member of a deflectable catheter can have any suitable length. Skilled artisans will be able to select a suitable length for a flexible member of a deflectable catheter according to a particular embodiment based on various considerations, including the degree of curvature intended to be accomplished when the deflectable catheter is in the second configuration. Example lengths considered suitable for a flexible member of a deflectable catheter include lengths equal to 1.0 centimeter, equal to about 1.0 centimeter, equal to between 0.5 centimeters and 1.5 centimeters, equal to between about 0.5 centimeters and about 1.5 centimeters, and any other length considered suitable for a particular embodiment.

The tubular member 404 is attached to the distal end 414 of the second shaft 402 and has a proximal end 420, a distal end 422, and a body that defines a lumen 424. The lumen 424 defined by the tubular member 404 extends from the proximal end 420 of the tubular member 404 to the distal end 422 of the tubular member 404 and is in communication with each of the first lumen 416 and second lumen 418 defined by the second shaft 402. In the embodiment shown, a portion of the second shaft 402 is disposed within the lumen 424 defined by the tubular member 404 and the proximal end 420 of the tubular member 404 is disposed over a portion of the exterior surface of the second shaft 402. The tubular member 404 is attached to the second shaft 402 using an adhesive. However, alternative embodiments can include a tubular member that is attached to the distal end of a shaft, or embedded within the material that forms a shaft. Alternatively, a tubular member can be directly attached to a flexible member. For example, a tubular member can have a proximal end and/or distal end that is attached to the proximal end or distal end of a flexible member, disposed over a portion of a flexible member, or within a passageway defined by a flexible member, and attached to the flexible member. Alternatively, a tubular member can have a proximal end attached to the distal end of a shaft, a distal end attached to the proximal end of a shaft, a proximal end embedded within the material that forms a shaft, and/or a distal end embedded within the material that forms a shaft.

The third shaft 406 is attached to the tubular member 404 and has a proximal end 430, a distal end 432, and a body that defines a first lumen 434 and a second lumen 436. Each of the first lumen 434 and the second lumen 436 extends from the proximal end 430 of the third shaft 406 to the distal end 432 of the third shaft 406. The first lumen 434 has a diameter that is greater than the diameter of the second lumen 436. The first lumen 434 is sized and configured to receive a portion of the imaging device 218, data transfer cable 220, first optical fiber 222, second optical fiber 224, irrigation tube 225, and/or safety wire 410. The second lumen 436 is sized and configured to receive a portion of the wire member 216. Each of the first lumen 434 and second lumen 436 defined by the third shaft 406 is in communication with the lumen 424 defined by the tubular member 404. In the embodiment illustrated, the second lumen 436 defined by the third shaft 406 is disposed on a third shaft lengthwise axis that is parallel to the lengthwise axis 211 of the deflectable catheter 208 and opposably positioned from an axis that contains the first lumen 236 defined by the first shaft 228 and the first lumen 416 defined by the second shaft 402 relative to the lengthwise axis 211. Thus, the second lumen 436 defined by the third shaft 406 is opposably positioned from the first lumen 416 defined by the second shaft 402 relative to the lengthwise axis 211.

In the embodiment illustrated, the third shaft 406 is attached to the distal end of the tubular member 404 such that a portion of the third shaft 406 is disposed within the lumen 424 defined by the tubular member 404 and the distal end 422 of the tubular member 404 is disposed over a portion of the exterior surface of the third shaft 406. The tubular member 404 is attached to the third shaft 406 using an adhesive. However, alternative embodiments can include a tubular member that is attached to the distal end of a shaft, or embedded within the material that forms a shaft.

The second flexible member 408 is attached to the distal end 432 of the third shaft 406 and has a proximal end 440, a distal end 442, a length 443, and defines a passageway 444. The length 443 of the second flexible member 408 extends from the proximal end 440 to the distal end 442 of the second flexible member 408. In the embodiment shown, the proximal end 440 is disposed over a portion of the exterior surface of the third shaft 406 and is attached to third shaft 406 using an adhesive. However, alternative embodiments can include a second flexible member that is attached to the distal end of the third shaft, or embedded within the material that forms the third shaft. The passageway 444 is in communication with each of the first lumen 434 and second lumen 436 defined by the third shaft 406.

The second shaft 402, tubular member 404, third shaft 406, and second flexible member 408 can be formed of any suitable material and can be fabricated using any suitable method of manufacture. Skilled artisans will be able to select a suitable material to form a second shaft, a tubular member, a third shaft, and a second flexible member and a suitable method of manufacture according to a particular embodiment based on various considerations, including the desired flexibility of the elongate member. Example materials considered suitable to form a second shaft, a tubular member, a third shaft, and a second flexible include biocompatible materials, materials that can be made biocompatible, metals such as stainless steel, titanium, nickel-titanium alloy (e.g., Nitinol), polymers, Pebax, nylon, polyethylene, polyurethane, silicone, coiled materials, braided materials, and any other material considered suitable for a particular application. Example methods of manufacture considered suitable to fabricate a second shaft, a tubular member, a third shaft, and a second flexible include extrusion processes, molding processes, and any other method considered suitable for a particular application.

For example, the first shaft 228, second shaft 402, tubular member 404, and third shaft 406 can be formed of a first material and the first flexible member 229 and second flexible member 408 can be formed of a second material. The first material can be the same as, or different than, the second material. For example, the shaft of a deflectable catheter can be formed of a material that has a first durometer hardness and a flexible member of the deflectable catheter can be formed of a material that has a second durometer harness that is less than the first durometer harness. In the embodiment illustrated, each of the first flexible member 229 and the second flexible member 408 is relatively more flexible than the first shaft 228, second shaft 402, tubular member 404, and third shaft 406.

Any suitable structure and/or material can be used to form a flexible member of an elongate member. Skilled artisans will be able to select a suitable structure and material to form a flexible member of an elongate member according to a particular embodiment based on various considerations, including the degree of curvature intended to be achieved when the deflectable catheter is in a second configuration. In the illustrated embodiment, each of the first flexible member 229 and the second flexible member 408 is a stainless steel (e.g., medical grade) compression spring that defines a helical configuration that extends from the proximal end of the flexible member to the distal end of the flexible member. The use of compression springs provides a mechanism for returning the elongate member 212 to its first, straight, configuration after it has achieved a second, curved, configuration. Alternative structures and/or materials considered suitable to form a flexible member include helical cut nickel-titanium alloy (e.g., Nitinol) segments, helical cut polymer segments, and any other structure and/or material considered suitable for a particular embodiment. A flexible member included in a deflectable catheter can be formed of any material capable of moving between first and second configurations and returning to its first configuration when no force is being applied to the flexible member.

In the illustrated embodiment, the cap 230 is attached to the distal end 442 of the second flexible member 408 such that the wire member opening 250 is opposably positioned from the first lumen 236 of the first shaft 228 relative to the lengthwise axis 211 of the deflectable catheter 208. In the embodiment shown, the proximal end 245 of the cap 230 is disposed within the passageway 444 defined by the second flexible member 408 and is attached to second flexible member 408 using an adhesive. However, alternative embodiments can include a cap that is attached to the distal end of the second flexible member, or embedded within the material that forms the second flexible member. In the embodiment illustrated, the shaft 247 of the cap 230 is entirely disposed within the passageway 444 defined by the second flexible member 408 such that the flange 248 is adjacent to, and contacts, the distal end 242 of the second flexible member 408. Alternatively, the shaft of a cap can be partially disposed within a passageway defined by a flexible member such that the second flexible member does not contact the flange of a cap.

In the illustrated embodiment, the distal end 432 of the third shaft 406 is disposed from the proximal end 245 of the cap 230 a distance 437 as measured when the deflectable catheter 208 is in the straight configuration. In the embodiment illustrated, the distance 437 is equal to 20.0 millimeters. While the distal end 432 of the third shaft 406 has been illustrated as disposed from the proximal end 245 of the cap 230 a distance 437, the distal end of a third shaft can be disposed any suitable distance from the proximal end of a cap when a deflectable catheter is in the straight configuration. Skilled artisans will be able to select a suitable distance between the distal end of a third shaft and the proximal end of a cap according to a particular embodiment based on various considerations, including the degree of curvature intended to be accomplished when a deflectable catheter is in the second configuration. Example distances considered suitable between the distal end of a third shaft and the proximal end of a cap include distances equal to 20.0 millimeters, equal to about 20.0 millimeters, equal to between 10.0 millimeters and 30.0 millimeters, equal to between about 10.0 millimeters and about 30.0 millimeters, and any other distance considered suitable for a particular embodiment. For example, a first embodiment of a deflectable catheter can have a first distance disposed between the distal end of a third shaft and the proximal end of a cap and a second embodiment of a deflectable catheter can have a second distance disposed between the distal end of a third shaft and the proximal end of a cap that is less than the first distance. The first embodiment can define a radius of curvature in the second configuration that is less than a radius of curvature that the second embodiment can define when it is in the second configuration. Thus, by increasing the distance between the distal end of a shaft and the proximal end of another shaft, the radius of curvature can be decreased.

The second flexible member 408 has a length 443 that is greater than the distance 437 between the distal end 432 of the third shaft 406 and the proximal end 245 of the cap 230. In the embodiment illustrated, the second flexible member has a length 443 that is equal to 27.0 millimeters. However, alternative embodiments can include a second flexible member that has a length that is less than, equal to, or substantially equal to, the distance between the distal end of a third shaft and the proximal end of a cap. While the second flexible member 408 has been illustrated as having a particular length 443, a flexible member of a deflectable catheter can have any suitable length. Skilled artisans will be able to select a suitable length for a flexible member of a deflectable catheter according to a particular embodiment based on various considerations, including the degree of curvature intended to be accomplished when the deflectable catheter is in the second configuration. Example lengths considered suitable for a flexible member of a deflectable catheter include lengths equal to 27.0 millimeters, equal to about 27.0 millimeters, equal to between 17.0 millimeters and 37.0 millimeters, equal to between about 17.0 millimeters and about 37.0 millimeters, and any other length considered suitable for a particular embodiment.

While deflectable catheter 208 has been illustrated as including a first shaft 228, a first flexible member 229, a second shaft 402, a tubular member 404, a third shaft 406, and a second flexible member 408, a deflectable catheter can include any suitable number of shafts, flexible members, and/or tubular members. Skilled artisans will be able to select a suitable number of shafts, flexible members, and/or tubular members to include on a deflectable catheter according to a particular embodiment based on various considerations, including the desired number of curves intended to be defined by the deflectable catheter when in the second configuration. Example number of shafts, flexible members, and/or tubular members considered suitable to include on a deflectable catheter include one, at least one, two, a plurality, and any other number considered suitable for a particular embodiment.

While the second shaft 402 has been described as being adhesively attached to the first flexible member 229, the tubular member 404 has been described as being adhesively attached to the second shaft 402, the third shaft 406 has been described as being adhesively attached to the tubular member 404, the second flexible member 408 has been described as being adhesively attached to the third shaft 406, and the cap 230 has been described as being adhesively attached to the second flexible member 408, a first component of an elongate member can be attached to a second component of the elongate member using any suitable structure for, or method of, attachment between two components. Skilled artisans will be able to select a suitable structure for, or method of, attachment between a first component of an elongate member and a second component of the elongate member according to an embodiment based on various considerations, including the materials that form the first component and/or the second component. Example structures for, and methods of, attachment between a first component of an elongate member and a second component of the elongate member considered suitable include using an adhesive, welding, fusing (e.g., heat fusing), using threaded connections, and any other structure or method of attachment considered suitable for a particular embodiment.

Figure 15:
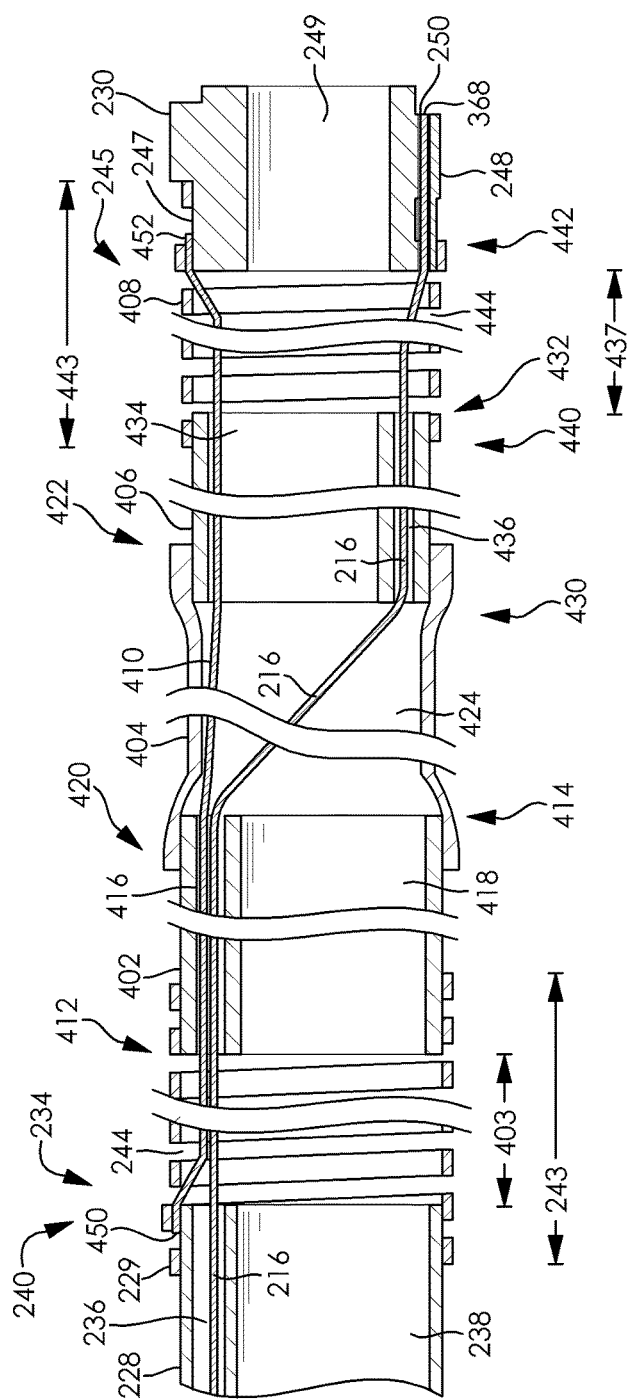
FIG. 15 is a partial sectional view of the deflectable catheter illustrated in FIG. 10, taken along the lengthwise axis of the deflectable catheter.
Figure 16:
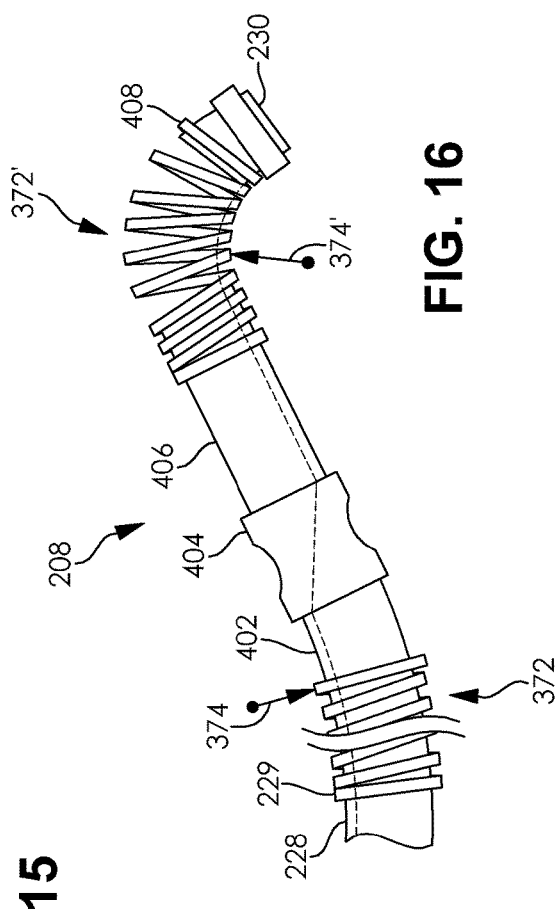
FIG. 16 is a partial side view of the deflectable catheter illustrated in FIG. 10 in a second configuration.

As shown in FIG. 15, the safety wire 410 has a first end 450 and a second end 452. The first end 450 is attached to the proximal end 240 of the first flexible member 229 and the second end 452 is attached to the distal end 442 of the second flexible member 408. In the embodiment illustrated, the safety wire 410 is soldered to the flexible members. Alternative embodiments can include a safety wire that is attached to a shaft in combination with, or independent of, attachment of the safety wire to the flexible member. While the safety wire 410 has been illustrated as being attached to the proximal end 240 of the first flexible member 229 and the distal end 442 of the second flexible member 408, a safety wire can be attached to any suitable portion of a flexible member, shaft, and/or cap. Example locations considered suitable to attach a first end of a safety wire include at the distal end of a first shaft, on the exterior surface of the first shaft between the proximal end and the distal end of a first shaft, on the interior surface of the first shaft between the proximal end and the distal end of a first shaft, to the proximal end of a first flexible member, between the proximal end and the distal end of a first flexible member, at the proximal end of a second shaft, on the exterior surface of the second shaft between the proximal end and the distal end of a second shaft, on the interior surface of the second shaft between the proximal end and the distal end of a second shaft, to the distal end of a first flexible member, and/or any other location considered suitable for a particular embodiment. Example locations considered suitable to attach a second end of a safety wire include at the distal end of a cap, on the exterior surface of a cap between the proximal end and the distal end of the cap, on the interior surface of a cap between the proximal end and the distal end of the cap, to the distal end of a second flexible member, between the proximal end and the distal end of a second flexible member, at the distal end of a third shaft, on the exterior surface of a third shaft between the proximal end and the distal end of the third shaft, on the interior surface of a third shaft between the proximal end and the distal end of the third shaft, to the proximal end of a second flexible member, and/or any other location considered suitable for a particular embodiment.

The safety wire 410 provides a mechanism for limiting, or substantially limiting, the amount of deformation (e.g., extension) that can be produced on the elongate member 212 when tension is applied to deflectable catheter 208. While the safety wire 410 has been illustrated as attached to the proximal end 240 of the first flexible member 229 and the distal end 442 of the second flexible member 408, other configurations are considered suitable. Example configurations considered suitable for the safety wire include attaching the first end of a safety wire to the proximal end of the first flexible member and the second end of the safety wire to the distal end of the first flexible member, attaching the first end of a safety wire to the proximal end of the first flexible member and the second end of the safety wire to the proximal end of the second flexible member, attaching the first end of a safety wire to the distal end of the first flexible member and the second end of the safety wire to the distal end of the second flexible member, attaching the first end of a safety wire to the proximal end of the second flexible member and the second end of the safety wire to the distal end of the second flexible member, and any other configuration considered suitable for a particular embodiment. Optionally, the safety wire 410 can be omitted from the deflectable catheter 208. Optionally, any of the lumens and/or passageways described herein can be sized and configured to receive a portion of a safety wire in addition to any other device, or component, described herein as disposed within the lumen. Optionally, more than one (e.g., two, a plurality) safety wire can be included in a deflectable catheter. For example, a first safety wire can extend along the length of a first flexible member and a second safety wire can extend along the length of a second flexible member. The first safety wire can have a first end attached to the proximal end of the first flexible member, and/or the distal end of a first shaft, and a second end attached to the distal end of the first flexible member, and/or the proximal end of a second shaft. The second safety wire can have a first end attached to the proximal end of the second flexible member, and/or the distal end of a third shaft, and a second end attached to the distal end of the second flexible member, and/or the proximal end of a fourth shaft, tubular member, or cap.

The safety wire 410 can have any suitable diameter and be formed of any suitable material, and skilled artisans will be able to select a suitable diameter and material for a safety wire according to a particular embodiment based on various considerations, including the degree of tension desired to be applicable to a deflectable catheter. Example materials considered suitable to form a safety wire include biocompatible materials, materials that can be made biocompatible, metals such as stainless steel, titanium, nickel-titanium alloy (e.g., Nitinol), polymers, Pebax, nylon, polyethylene, polyurethane, silicone, coiled materials, braided materials, and any other material considered suitable for a particular application. The safety wire can have any suitable structural configuration. Example structural configurations considered suitable for a safety wire include cross-sectional configurations that are round, rectangular (e.g., flat wire), and any other structural configuration considered suitable for a particular embodiment.

While the safety wire 410 has been illustrated as extending through the passageway 244 defined by the first flexible member 229, through the first lumen 416 defined by the second shaft 402, through the lumen 424 defined by the tubular member 410, through the first lumen 434 defined by the third shaft 406, and through the passageway 444 defined by the second flexible member 408, a flexible member can extend through any suitable lumen and/or passageway described herein. For example, in an alternative embodiment, a safety wire can extend through the passageway defined by a first flexible member, through the second lumen defined by a second shaft, through the lumen defined by a tubular member, through the second lumen defined by a third shaft, and through the passageway defined by a second flexible member.

While the safety wire 410 has been described as being soldered to each of the first flexible member 229 and the second flexible member 408, a safety wire can be attached to any portion of an elongate member using any suitable structure for, or method of, attachment between two components. Skilled artisans will be able to select a suitable structure for, or method of, attachment between a safety wire and a component of an elongate member according to an embodiment based on various considerations, including the materials that form the safety wire and the component to which the safety wire is intended to be attached. Example structures for, and methods of, attachment between a safety wire and a component of an elongate member considered suitable include using an adhesive, welding, fusing (e.g., heat fusing), using threaded connections, and any other structure or method of attachment considered suitable for a particular embodiment.

In the illustrated embodiment, when the deflectable catheter 208 is in the first, straight configuration, the first lumen 236 defined by the first shaft 228 and the first lumen 416 defined by the second shaft 402 are disposed on a first plane that contains the lengthwise axis 211 of the deflectable catheter 408. When the deflectable catheter 208 is in the first, straight configuration, each of the second lumen 436 defined by the third shaft 406, the wire member second end 368, and the wire member opening 250 defined by the cap 230 is disposed on a second plane that contains the lengthwise axis 211 of the deflectable catheter 208. In the illustrated embodiment, the first plane and the second plane are coplanar and the first lumen 236 defined by the first shaft 228 and the first lumen 416 defined by the second shaft 402 are opposably positioned from the second lumen 436 defined by the third shaft 406, the wire member second end 368, and the wire member opening 250 defined by the cap 230 relative to a plane that contains the lengthwise axis 211 of the deflectable catheter 208 and that is disposed orthogonal to the first plane and the second plane. Thus, the first lumen 236 defined by the first shaft 228 and the first lumen 416 defined by the second shaft 402 are opposably positioned from the second lumen 436 defined by the third shaft 406, the wire member second end 368, and the wire member opening 250 defined by the cap 230 relative to the lengthwise axis 211.

While the first plane that contains the first lumen 236 defined by the first shaft 228 and the first lumen 416 defined by the second shaft 402 and the second plane that contains the second lumen 436 defined by the third shaft 406, the wire member second end 368, and the wire member opening 250 defined by the cap 230 have been described as coplanar, the first plane and second plane can be positioned at any suitable angle relative to one another and include any suitable feature described herein. Skilled artisans will be able to select a suitable angle to position a first plane that contains one or more features of an elongate member relative to a second plane that includes one or more features of an elongate member according to a particular embodiment based on various considerations, including the structural arrangement of the bodily passage within which a deflectable catheter is intended to be used. Example angles considered suitable to position a first plane (e.g., that contains the first lumen 236, distal end of the first lumen 236, first lumen 416 defined by the second shaft 402, and/or distal end of the first lumen 416 defined by the second shaft 402) and a second plane (e.g., that contains the second lumen 436 defined by the third shaft 406, the distal end of the second lumen 436 defined by the third shaft 406, the wire member second end 368, and/or the wire member opening 250 defined by the cap 230) include positioning the first plane and the second plane such that they are coplanar, orthogonal to one another, or such that the angle disposed between the first plane and the second plane is an angle equal to about 45 degrees, an angle between about 1 degree and about 90 degrees, an angle about 90 degrees, an angle between about 90 degrees and about 180 degrees, an angle between about 180 degrees and about 270 degrees, an angle between about 270 degrees and about 360 degrees, an angle equal to, substantially equal to, great than, or less than, 45 degrees, 90 degrees, 180 degrees, 270 degrees, and any other angle considered suitable for a particular application.

The first end of wire member 216 is attached to the actuator 262 and extends from the first end of the wire member 216 through the first lumen 236 defined by the first shaft 228, through the passageway 244 defined by the first flexible member 229, through the first lumen 416 defined by the second shaft 402, through the lumen 424 defined by the tubular member 404 such that is passes through a plane that contains the lengthwise axis 211 of the deflectable catheter 208, through the second lumen 436 defined by the third shaft 406, through the passageway 444 defined by the second flexible member 408, and is attached to cap 230 within wire member opening 250 (e.g., using an adhesive, welding). However, other methods of attachment, such as those described herein, are considered suitable. In the illustrated embodiment, the wire member 216 is disposed between the second flexible member 408 and the exterior surface of the cap 230 from the proximal end 245 of the cap 230 to the flange 248.

Each of the data transfer cable 220, first optical fiber 222, second optical fiber 224, and irrigation tube 225 extends from the handle 214 through the second lumen 238 of the first shaft 228, the passageway 244 defined by the first flexible member 229, the second lumen 418 defined by the second shaft 402, the lumen 424 defined by the tubular member 404, the first lumen 434 defined by the third shaft 406, the passageway 444 defined by the second flexible member 408 and is attached to the imaging device 218 or cap 230, as described herein. The imaging device 218 is attached to the data transfer cable 220, disposed within the passageway 249 defined by the cap 230, and is attached to the cap 230 (e.g., using adhesive, welding). The first optical fiber 222 is disposed between the second flexible member 408 and the exterior surface of the cap 230 from the proximal end 245 of the cap 230 to the first optical fiber opening 251 and is attached to the cap 230 (e.g., using adhesive). The second optical fiber 224 is disposed between the second flexible member 408 and the exterior surface of the cap 230 from the proximal end 245 of the cap 230 to the second optical fiber opening 252 and is attached to the cap 230 (e.g., using adhesive). The irrigation tube 225 is disposed between the second flexible member 408 and the exterior surface of the cap 230 from the proximal end 245 of the cap 230 to the irrigation tube opening 253 and is attached to the cap 230 (e.g., using adhesive) such that the second end 192 of the irrigation tube 225 is directed toward the imaging device 218.

Figure 22:
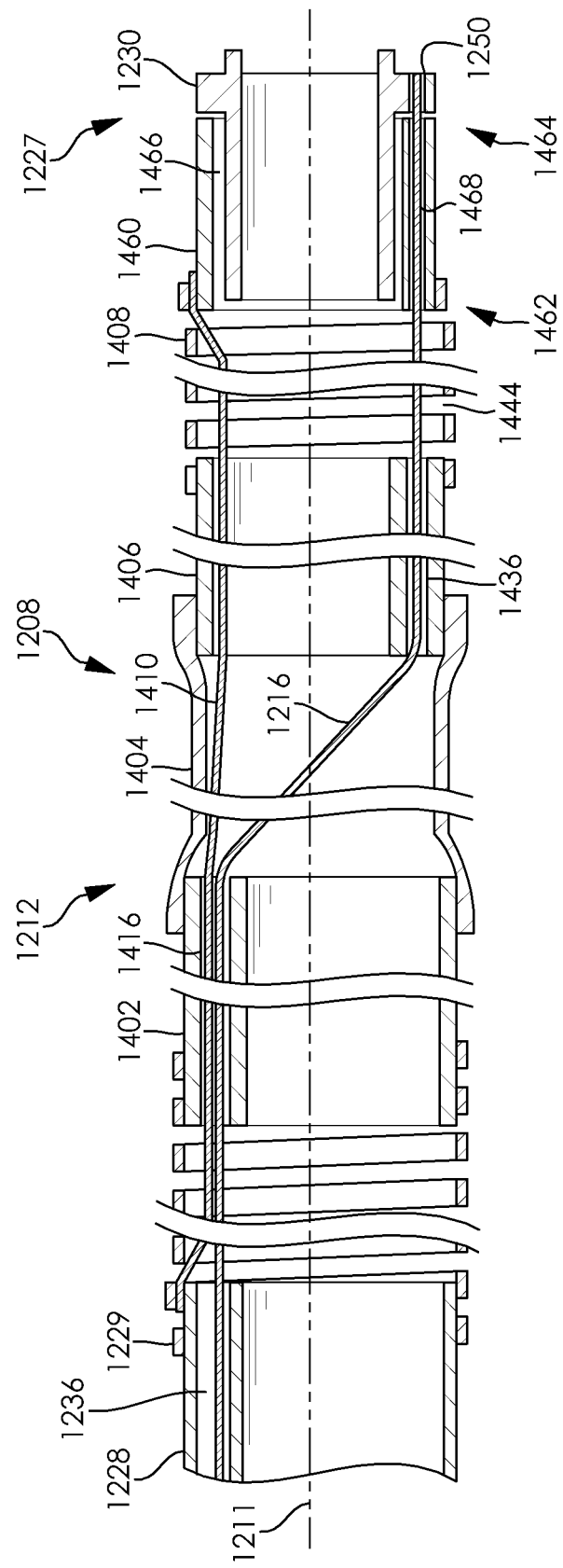
FIG. 22 is a partial sectional view of another deflectable catheter.

While each of the wire member 216, first optical fiber 222, second optical fiber 224, and irrigation tube 225 has been illustrated and described as disposed between the interior surface of the second flexible member 408 and the exterior surface of the cap 230, other structural arrangements are considered suitable. For example, alternative embodiments can include a tubular member that is attached to the shaft of a cap such that the exterior surface of the tubular member is attached to a second flexible member and each of the wire member, first optical fiber, second optical fiber, and irrigation tube is disposed within the tubular member, disposed between the interior surface of the tubular member and the shaft of the cap, and extend to an opening defined by the flange of the cap, as described herein. Alternatively, a dual lumen shaft can be attached to the shaft of a cap such that the exterior surface of the dual lumen shaft is attached to a second flexible member and the wire member is disposed in a first lumen defined by the dual lumen shaft and each of the first optical fiber, second optical fiber, and irrigation tube is disposed in a second lumen defined by the dual lumen shaft. The dual lumen shaft can be attached to the cap such that the lumen in which the wire member is disposed is coaxial with the wire member opening defined by the cap. This is illustrated in FIG. 22. Each of the first optical fiber, second optical fiber, and irrigation tube extends through the second lumen defined by the dual lumen shaft and is disposed between the interior surface of the second lumen defined by the dual lumen shaft and the exterior surface of the shaft of the cap, and extend to an opening defined by the flange of the cap, as described herein.

In use, movement of actuator 262 away from elongate member distal end 227, as shown by arrow 370 in FIG. 10, from the actuator first position, as shown in FIG. 10, in a proximal direction to the actuator second position (not shown) causes the wire member 216 to move in a proximal direction such that wire member first end (not shown) advances away from the distal end 227 of the elongate member 212. This creates tension in the wire member 216 that results in movement of wire member second end 368 and elongate member 212 such that elongate member 212 moves from a straight configuration, as shown in FIG. 10, to a curved configuration, as shown in FIG. 16, in which elongate member 212 defines a first curve 372 at a first radius of curvature 374 and a second curve 372' at a second radius of curvature 374'. In the embodiment illustrated, the first radius of curvature 374 is greater than the second radius of curvature 374' such that the first curve 372 provides less deflection than the second curve 372' when the elongate member 212 is in the second, curved, configuration. Movement of actuator 262 toward elongate member distal end 228, in a direction opposite that of arrow 370, reduces, or eliminates, tension in wire member 216 and results in elongate member 212 returning to the straight configuration. Thus, when actuator 262 is in the actuator first position, elongate member 212 is in the straight configuration and when actuator 262 is in the actuator second position, elongate member 212 is in the curved configuration.

When elongate member 212 is in the curved configuration, the portion of elongate member 212 disposed distal to the first curve 374 is disposed at an angle (e.g., less than 180 degrees) to the portion of the elongate member 212 disposed proximal to the first curve 374 relative to an axis that is parallel to the lengthwise axis 211 of the deflectable catheter 208. In addition, when elongate member 212 is in the curved configuration, the portion of the elongate member 212 disposed distal to the second curve 374' is disposed at an angle (e.g., less than 270 degrees) to the portion of the elongate member 212 disposed proximal to the second curve 374' relative to an axis that is parallel to the lengthwise axis 211 of the deflectable catheter 208. The portion of an elongate member disposed distal to a curve can be disposed at any suitable angle to the portion of the elongate member disposed proximal to the curve, and skilled artisans will be able to select a suitable angle according to a particular embodiment based on various considerations, including the procedure intended to be performed. Example angles considered suitable to define between a portion of an elongate member disposed distal to a curve and a portion of an elongate member disposed proximal to the curve include angles between about 0 degrees and 180 degrees, about 45 degrees, about 90 degrees, about 120 degrees, equal to, substantially equal to, greater than, or less than, 45 degrees, 90 degrees, 120 degrees, and any other angle considered suitable for a particular application.

The radii of curvature 374, 374' defined by the elongate member 212 can vary and be based upon at least the material(s) that forms the elongate member 212, the location of the actuator second position, the length of elongate member 212, the length of wire member 216, the axial length of actuator opening as it relates to the length of elongate member 212, the distance between the distal end 234 of the first shaft 228 and the proximal end 412 of the second shaft 402, and/or the distance between the distal end 432 of the third shaft 406 and the proximal end 245 of the cap 230. For example, by increasing the distance between the distal end of a first shaft and the proximal end of a second shaft and/or the distance between the distal end of a third shaft and the proximal end of a cap, the amount of deflection can be increased and radius of curvature can be reduced. Movement of an elongate member 212 between a straight configuration and a curved configuration allows the deflectable catheter 208 to be advanced through tortuous bodily passages, such as airways, sinus cavities, and/or sinus passages. In addition, movement between a straight and curved configuration allows for the elongate member 212 to be manipulated such that distal end 227 of the elongate member 212 can be positioned in various configurations to view various aspects of a bodily passage (e.g., during the performance of a sleep study).

Various methods are described herein. While the methods described herein are shown and described as a series of acts, it is to be understood and appreciated that the methods are not limited by the order of acts, as some acts may, in accordance with these methods, occur in different orders, and/or concurrently with other acts described herein.

Figure 17:
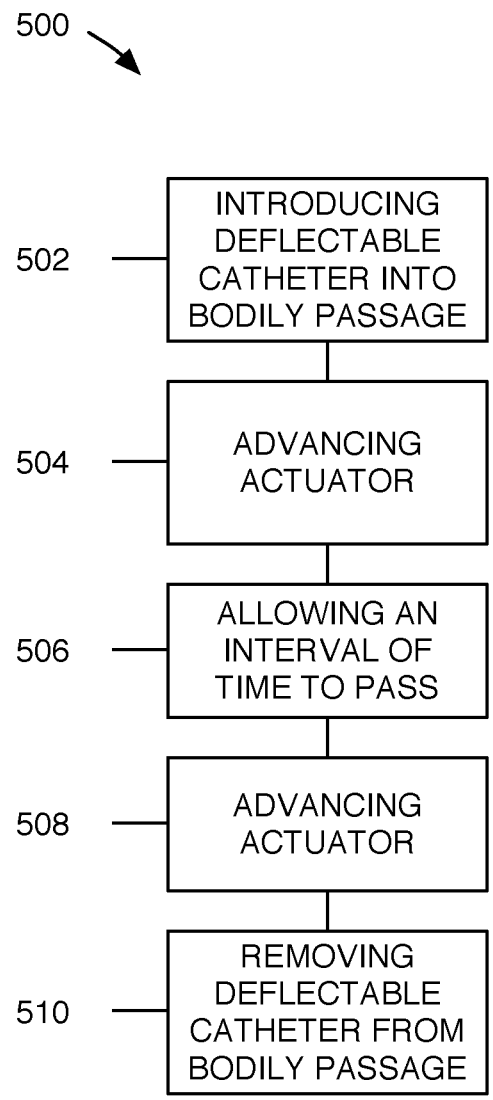
FIG. 17 is a flowchart representation of a method of visualizing a bodily passage using a deflectable catheter.

FIG. 17 is a flowchart representation of an exemplary method 500 of visualizing a bodily passage.

A step 502 comprises introducing a deflectable catheter that has a deflectable catheter proximal end and a deflectable catheter distal end into a bodily passage such that the deflectable catheter distal end is disposed in the bodily passage. The deflectable catheter comprises an elongate member, an actuator, and a wire member. Another step 504 comprises advancing the actuator from an actuator first position to an actuator second position to define a curve along the length of the elongate member within the bodily passage. Another step 506 comprises allowing an interval of time to pass. Another step 508 comprises advancing the actuator from the actuator second position to the actuator first position. Another step 510 comprises removing the deflectable catheter from the bodily passage.

Step 502 can be accomplished by applying a proximal and/or distally directed force on any suitable portion of a deflectable catheter such that it is introduced into a bodily passage.

Step 502 can be accomplished using any suitable deflectable catheter or deflectable catheter system, and skilled artisans will be able to select a suitable deflectable catheter or deflectable catheter system according to a particular embodiment based on various considerations, including the procedure intended to be performed. Example deflectable catheters considered suitable to perform method 500 include deflectable catheter 8, deflectable catheter 208, and any other deflectable catheter considered suitable for a particular embodiment. Example deflectable catheter systems considered suitable to perform method 500 include deflectable catheter system 602, and any other deflectable catheter system considered suitable for a particular embodiment. An example deflectable catheter that can be used to accomplish the methods, steps, optional steps, and/or alternative steps described herein is deflectable catheter 208 and is illustrated and described with respect to FIGS. 10, 11, 12, 13, 14, 15, and 16.

Furthermore, while method 500 has been described as introducing a deflectable catheter into a bodily passage, it is considered suitable to deploy a deflectable catheter into any suitable bodily passage. Skilled artisans will be able to select a suitable bodily passage to deploy a deflectable catheter according to a particular embodiment based on various considerations, including the procedure intended to be performed. Example bodily passages considered suitable include, but are not limited to, sinus passages, airways, sinus cavities, and any other bodily passage considered suitable for a particular application.

Step 504 can be accomplished by applying a proximally directed force on the actuator such that it moves from the actuator first position to the actuator second position. The application of a proximally directed force on the actuator axially advances the wire member in the proximal direction such that the elongate member moves from a straight, or substantially straight, configuration, to a curved configuration in which elongate member defines one or more curves along its length. Alternatively, step 504 can comprise advancing the actuator from the actuator first position to a position between the actuator first position and the actuator second position. Alternatively, step 504 can be completed such that the elongate member defines a curve outside of the bodily passage.

Step 506 can be accomplished by completing step 502 and/or step 504 and waiting for an interval of time to pass before completing step 508 and/or step 510. Any suitable interval of time is considered suitable, and skilled artisans will be able to select a suitable interval of time according to a particular embodiment based on various considerations, including the procedure being performed. Example intervals of time considered suitable include, but are not limited to, allowing one or more seconds to pass, one or more minutes to pass, one or more hours to pass, one or more days to pass, and any other interval of time considered suitable for a particular application.

An optional step comprises adjusting the position of the elongate member distal end within the bodily passage. This can be accomplished by applying a force on the actuator such that it moves between the actuator first position and actuator second position and/or applying a force on the deflectable catheter such that is advanced into or withdrawn from the bodily passage.

Step 508 can be accomplished by applying a distally directed force on the actuator such that it moves from the actuator first position to the actuator second position. The application of a distally directed force on the actuator axially advances the wire member in the distal direction such that the elongate member moves from a curved configuration in which elongate member defines one or more curves along its length to a straight, or substantially straight, configuration. Alternatively, step 508 can comprise advancing the actuator from the actuator second position, or a position between the actuator second position and the actuator first position, to a position between the actuator first position and the actuator second position. Optionally, step 508 can be omitted from method 500.

Step 510 can be accomplished by placing a proximally and/or distally directed force on any suitable portion of a deflectable catheter such that it is withdrawn from the bodily passage.

An optional step comprises confirming placement of the elongate member and/or that the elongate member defines one or more curves along its length. This optional step can be accomplished using any suitable structure or method of visualization, and skilled artisans will be able to select a suitable structure or method to visualize an elongate member according to a particular embodiment based on various considerations, such as the desired bodily passage within which a deflectable catheter is intended to be deployed. Example structures and methods of visualization include, but are not limited, using direct visualization, fluoroscopy, a scope, transcutaneously, taking an x-ray, and any other method considered suitable for a particular application.

Another optional step comprises performing treatment. This optional step can be completed using any suitable device, system, or component. For example, this optional step can be completed by performing a sleep study on a patient. Alternatively, or in combination with performing a sleep study, this optional step can be completed by introducing a fluid into the irrigation tube to flush a bodily passage, sinus passage, airway, and/or sinus cavity. Alternatively, or in combination with performing a sleep study, this optional step can be completed by applying suction to the irrigation tube to withdraw material within a bodily passage, sinus passage, airway, and/or sinus cavity. Another optional step comprises cleaning the imaging device. This optional step can be completed by introducing a fluid into the irrigation tube until the imaging device is clean.

While various steps, alternative steps, and optional steps have been described above with respect to visualizing a bodily passage, these steps, alternative steps, and optional steps can be included in, accomplished concurrently with, and/or accomplished in the alternative to, the method, steps, alternative steps, and/or optional steps described below with respect to method 1500.

FIGS. 18, 19, and 20, illustrate a deflectable catheter system 602 that comprises a proximal housing 603, a tubular member 604, and a deflectable catheter 608. The tubular member 604 is attached to the proximal housing 603 and the deflectable catheter 608. Deflectable catheter 608 is similar to the deflectable catheter 208 illustrated in FIGS. 10, 11, 12, 13, 14, 15, and 16, and described above, except as detailed below. Reference numbers in FIGS. 18, 19, and 20 refer to the same structural element or feature referenced by the same number in FIGS. 10, 11, 12, 13, 14, 15, and 16, offset by 400. Thus, the deflectable catheter 608 includes an elongate member 612, a handle 614, a wire member 616, an imaging device 618, a data transfer cable 620, a first optical fiber 622, a second optical fiber 624, and an irrigation tube 625.

While deflectable catheter system 602 has been illustrated as including deflectable catheter 608, a deflectable catheter system can include any suitable deflectable catheter, and skilled artisans will be able to select a suitable deflectable catheter to include in a deflectable catheter system according to a particular embodiment based on various considerations, including the procedure intended to be performed. Example deflectable catheters considered suitable to include in a deflectable catheter system include deflectable catheter 8, deflectable catheter 208, and any other deflectable catheter considered suitable for a particular embodiment.

In the illustrated embodiment, the deflectable catheter system 602 includes a first set of straps 605', a second set of straps 605'', a second data transfer cable 620', and a third data transfer cable 620''. In addition, the handle 614 defines the passageway 702'' on the proximal end of the handle 614. The passageway 702'' is sized and configured to receive a portion of tubular member 604. While, the passageway 702'' has been illustrated at the proximal end of the handle 614, a passageway defined by a handle can be defined at any suitable location on the handle, such as on a side, at the distal end, or at any other location considered suitable for a particular embodiment.

The proximal housing 603 has a proximal end 860, a distal end 862, and a body 864 that defines a chamber 866, an irrigation port 868, a first opening 870, and a second opening 872. The irrigation port 868 has a passageway 867 that is in communication with the chamber 866 and an end 873 that has a connector. The end 873 of the irrigation port 868 can include any suitable connector and/or adapter capable of attaching one or more devices to the irrigation port 868. Skilled artisans will be able to select a suitable connector and/or adapter to include on the end of an irrigation port according to a particular embodiment based on various considerations, including the materials that form the irrigation port. Example connectors and/or adapters considered suitable to include on an irrigation port include threaded connectors, Tuohy Borst adapters, luer lock connectors, and any other connector and/or adapter considered suitable for a particular embodiment.

Each of the first opening 870 and second opening 872 extends through the body 864 and provides access to the chamber 866. The first opening 870 is sized and configured to receive a portion of tubular member 604 and the second opening 872 is sized and configured to receive a portion of another device (e.g., communications device, HDMI cable, communication cable, power cable) and allow the device to pass through second opening 872 such that it can be attached to a control board (e.g., control board 664), or another device (e.g., data transfer cable). The proximal housing 603 can be attached at any suitable location during use. For example, the proximal housing 603 can be attached to a patient, to the bed of a patient, to a medical cart, or any other location.

The tubular member 604 has a proximal end 874, a distal end 876, and a body 878 that defines a lumen 880 that extends from the proximal end 874 to the distal end 876. The tubular member 604 is attached to the proximal housing 603 such that the lumen 880 defined by the tubular member 604 is in communication with the chamber 866 defined by the housing 603. The tubular member 604 is attached to the handle 614 such that the lumen 880 defined by the tubular member 604 is in communication with the housing chamber (not shown). The tubular member 604 can be attached to the proximal housing 603 and the handle 614 using any suitable method of attachment, such as adhesive. While the tubular member 604 has been described as being adhesively attached to the proximal housing 603 and the handle 614, a tubular member can be attached to a housing and a handle using any suitable structure for, or method of, attachment between two components. Skilled artisans will be able to select a suitable structure for, or method of, attachment between a tubular member and a housing and a handle according to an embodiment based on various considerations, including the materials that form the tubular member, housing, and/or handle. Example structures for, and methods of, attachment between a tubular member and a housing and tubular member and a handle considered suitable include using an adhesive, welding, fusing (e.g., heat fusing), using threaded connections, connectors and/or adapters, such as threaded connectors, Tuohy Borst adapters, luer lock connectors, and any other structure or method of attachment considered suitable for a particular embodiment.

A tubular member 604 can have any suitable length and outside diameter, and skilled artisans will be able to select a suitable length and outside diameter for a tubular member according to a particular embodiment based on various considerations, including the location at which a proximal housing is intended to be attached during use. Example lengths considered suitable for a tubular member include lengths between 100 centimeters and 300 centimeters, lengths between about 100 centimeters and 300 centimeters, lengths equal to, substantially equal to, less than, or greater than, 100 centimeters, 300 centimeters, and any other length considered suitable for a particular embodiment. Example outside diameters considered suitable for a tubular member include outside diameters between 2.0 millimeters and 6.0 millimeters, between about 2.0 millimeters and about 6.0 millimeters, outside diameters equal to, substantially equal to, less than, or greater than, 2.0 millimeters, 6.0 millimeters, and any other outside diameter considered suitable for a particular embodiment.

In the embodiment illustrated, the first end of the irrigation tube 625 is attached to the proximal housing 603 such that lumen 794 defined by the irrigation tube 625 is in communication with the lumen 867 defined by the irrigation port 868. The irrigation tube 625 extends through the lumen 880 defined by the tubular member 604, through the handle 614, through the elongate member 612, and is attached to the cap 630, as described herein. Thus, fluid can be introduced through the irrigation port 868 and through the irrigation tube 625.

The second data transfer cable 620' has a first end attached to the proximal end 860 of the proximal housing 603, extends through the tubular member 604, and has a second end attached to the control board housed within handle 614. The second data transfer cable 620' is attached to the control board such that data and/or power can be transmitted between the second data transfer cable and the control board. Thus, the second data transfer cable 620' is in signal communication with the control board. The third data transfer cable 620" has a first end 888 attached to the first end of the second data transfer cable 620' and a second end (not shown) that can be attached to any suitable device, component, and/or system. Thus, the third data transfer cable 620" is in signal communication with the second data transfer cable 620' and another device. For example, the second end of the third data transfer cable 620" can be attached to a control unit, such as the control units described in U.S. Nonprovisional application Ser. No. 14/191,535, filed Feb. 27, 2014, and entitled Medical Devices, Systems, and Methods for the Visualization and Treatment of Bodily Passages. Each of the second data transfer cable 620' and/or third data transfer cable 620" can comprise any suitable device capable of transmitting data and/or power, such as those described herein (e.g., HDMI cable, communication cable, power cable).

While the proximal housing 603 has been illustrated as having a particular structural arrangement, a proximal housing can have any suitable structural arrangement, and skilled artisans will be able to select a suitable structural arrangement for a proximal housing according to a particular embodiment based on various considerations, including the devices and/or components that are housed within the proximal housing. For example, a proximal housing can have any of the features described with respect to handle 14, handle 214, can define a first and/or second opening on the side of the proximal housing, and/or can be sized and configured to house a control board and/or any of the other devices, components, and/or features described with respect to handle 14 and/or handle 214, as described in more detail herein.

The first set of straps 605' provides a mechanism for attaching the proximal housing 603 to another structure (e.g., patient, bed of a patient, medical cart) and the second set of straps 605" provides a mechanism for attaching the handle 614 to another structure (e.g., patient, bed of patient, medical cart). The first set of straps 605' is attached to the proximal housing 603 and is sized and configured to attach the proximal housing 603 the bed of a patient. The second set of straps 605" is attached to the handle 614 and is sized and configured to attach the handle 614 to the bicep of a patient, or other suitable structure. Each strap of the plurality of straps can comprise any suitable length and/or structure capable of providing releasable attachment between the device on which the strap is attached and another structure. For example, a pair of mating straps can include hook and loop fasteners to provide releasable attachment. However, other forms of releasable attachment are considered suitable, such as using adhesive, or any other form of attachment considered suitable for a particular embodiment.

The deflectable catheter system 602 illustrated in FIGS. 18, 19, and 20 provides a mechanism for positioning the proximal housing 603 at a first location relative to a patient and positioning the handle 614 at a second location relative to a patient that is different than the first location. This configuration allows for deflection of the elongate member to be accomplished at the second location and irrigation to be accomplished at the first location.

FIG. 21 illustrates a cross-sectional view of another deflectable catheter system 902 that comprises a proximal housing attached to a deflectable catheter. The cross-sectional view has been taken along the length of the tubular member of the system that is disposed between the proximal housing and the handle (e.g., tubular member 604). The deflectable catheter system 902 is similar to the deflectable catheter system 602 illustrated in FIGS. 18, 19 and 20, and described above, except as detailed below. Reference numbers in FIG. 21 refer to the same structural element or feature referenced by the same number in FIGS. 18, 19, 20, and 21, offset by 300.

In the illustrated embodiment, the proximal housing houses the control board such that each of the data transfer cable 920, first light fiber 922, second light fiber 924, and the irrigation tube 925 extends from the chamber defined by the proximal housing, through the tubular member 904, through the handle, through the elongate member and is attached to the cap, as described herein.

FIG. 22 illustrates another deflectable catheter 1208. The deflectable catheter 1208 is similar to the deflectable catheter 208 illustrated in FIGS. 10, 11, 12, 13, 14, 15, and 16, and described above, except as detailed below. Reference numbers in FIG. 22 refers to the same structural element or feature referenced by the same number in FIGS. 10, 11, 12, 13, 14, 15, and 16, offset by 1000. The handle, imaging device, data transfer cable, first optical fiber, second optical fiber, and irrigation tube have been omitted from FIG. 22 for clarity. Thus, the deflectable catheter 1208 includes an elongate member 1212 and a wire member 1216.

In the illustrated embodiment, the elongate member 1212 has a proximal end (not shown), a distal end 1227, a first shaft 1228, a first flexible member 1229, a second shaft 1402, a tubular member 1404, a third shaft 1406, a second flexible member 1408, a safety wire 1410, a cap 1230, and a fourth shaft 1460.

In the illustrated embodiment, the fourth shaft 1460 is attached to the second flexible member 1408 and has a proximal end 1462, a distal end 1464, and a body that defines a first lumen 1466 and a second lumen 1468. Each of the first lumen 1466 and the second lumen 1468 extends from the proximal end 1462 of the fourth shaft 1460 to the distal end 1464 of the fourth shaft 1460. The first lumen 1466 has a diameter that is greater than the diameter of the second lumen 1468. The first lumen 1466 is sized and configured to receive a portion of the imaging device, data transfer cable, first optical fiber, second optical fiber, irrigation tube, safety wire, and/or cap 1230. The second lumen 1468 is sized and configured to receive a portion of the wire member 1216. Each of the first lumen 1466 and second lumen 1468 defined by the fourth shaft 1460 is in communication with the passageway 1444 defined by the second flexible member 1408. In the embodiment illustrated, the second lumen 1468 defined by the fourth shaft 1460 is disposed on an axis that is parallel to the lengthwise axis 1211 of the deflectable catheter 1208, is coaxial with an axis that extends through the second lumen 1436 defined by the third shaft 1406 and an axis that that extends through the wire member opening 1250, and is opposably positioned from an axis that extends through the first lumen 1236 defined by the first shaft 1228 and the first lumen 1416 defined by the second shaft 1402 relative to the lengthwise axis 1211. Thus, the second lumen 1468 defined by the fourth shaft 1460 is opposably positioned from the first lumen 1416 defined by the second shaft 1402 relative to the lengthwise axis 1211.

The cap 1230 is disposed within the first lumen 1466 defined by the fourth shaft 1460 and a portion of the exterior surface of the cap 1230 is attached to a portion of the interior surface of the fourth shaft 1460. In addition, the second flexible member 1408 is attached to a portion of the exterior surface of the fourth shaft 1460. The cap 1230 is attached to the fourth shaft 1460 using adhesive and the second flexible member 1408 is attached to the fourth shaft 1460 using adhesive.

While adhesive has been described as providing attachment between the cap 1230 and the fourth shaft 1460 and between the fourth shaft 1460 and the second flexible member 1408, a cap can be attached to a shaft and a flexible member can be attached to a shaft using any suitable structure for, or method of, attachment between two components. Skilled artisans will be able to select a suitable structure for, or method of, attachment between a cap and a shaft and between a flexible member and a shaft according to an embodiment based on various considerations, including the materials that form the shaft, flexible member, and/or cap. Example structures for, and methods of, attachment between a cap and a shaft and between a shaft and a flexible member considered suitable include using an adhesive, welding, fusing (e.g., heat fusing), using threaded connections, and any other structure or method of attachment considered suitable for a particular embodiment.

The wire member 1216 is disposed in, and extends through, the second lumen 1468 defined by the fourth shaft 1460 and is attached to the cap 1230 within wire member opening 1250. A portion of each of the first optical fiber, second optical fiber, and irrigation tube is disposed within the first lumen 1466 defined by the fourth shaft 1460 between the interior surface of the first lumen 1466 and the exterior surface of the shaft of the cap 1230. Each of the first optical fiber, second optical fiber, and irrigation tube extends through the first lumen 1466 defined by the fourth shaft 1460 to an opening defined by the flange of the cap 1230, as described herein.

Figure 23:
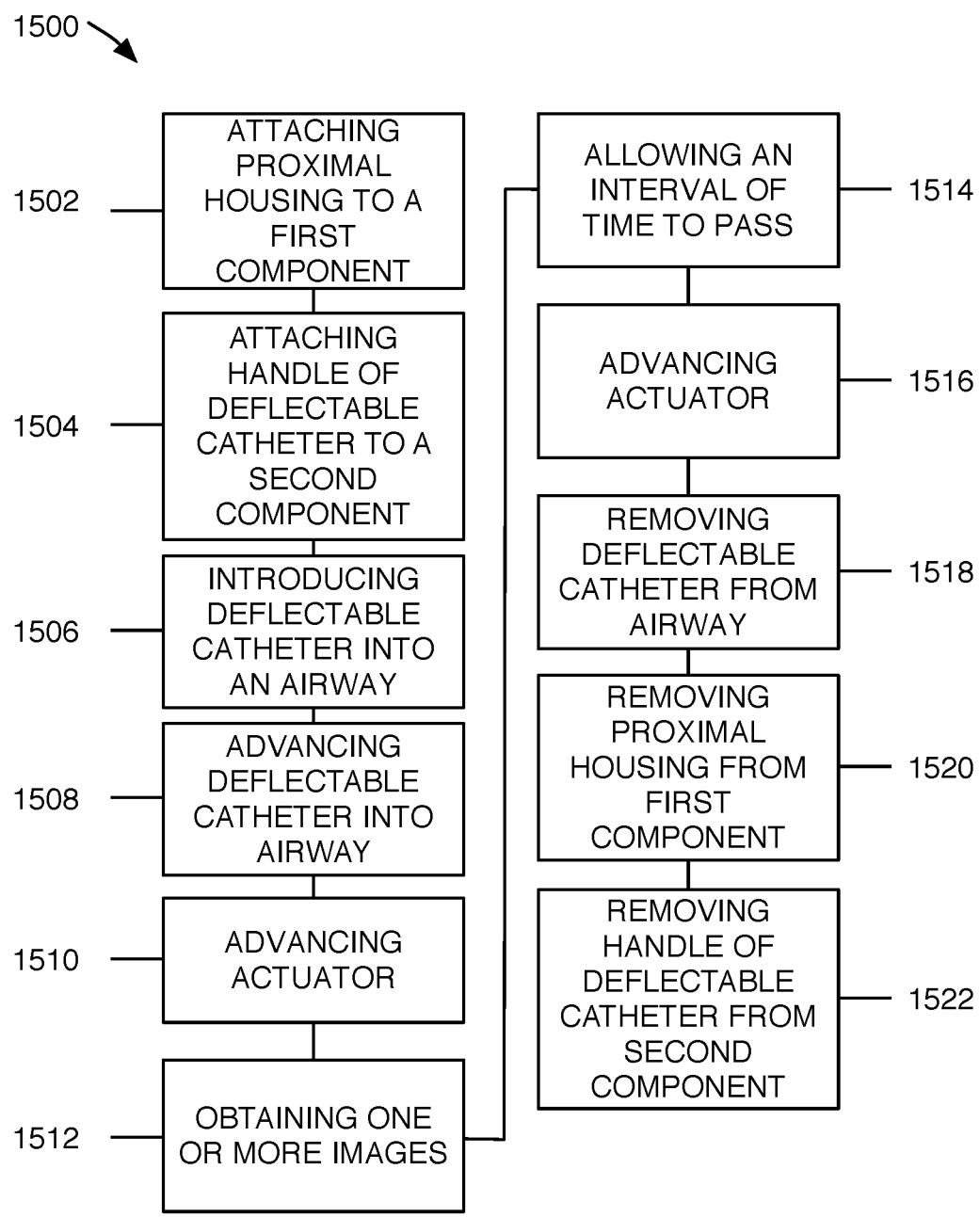
FIG. 23 is a flowchart representation of a method of visualizing a bodily passage using a deflectable catheter system.

FIG. 23 is a flowchart representation of an exemplary method 1500 of visualizing an airway using a deflectable catheter system.

A step 1502 comprises attaching a proximal housing to a first component. Another step 1504 comprises attaching the handle of a deflectable catheter to a second component that is different than the first component. The deflectable catheter has a proximal end and a distal end and comprises an elongate member, a handle, a wire member, an imaging device, a data transfer cable, a first optical fiber, a second optical fiber, and an irrigation tube. Another step 1506 comprises introducing the deflectable catheter into an airway such that the deflectable catheter distal end is disposed in the airway. Another step 1508 comprises advancing the deflectable catheter into the airway. Another step 1510 comprises advancing the actuator from an actuator first position to an actuator second position to define a curve along the length of the elongate member within the airway. Another step 1512 obtaining one or more images. Another step 1514 comprises allowing an interval of time to pass. Another step 1516 comprises advancing the actuator from the actuator second position to the actuator first position. Another step 1518 comprises removing the deflectable catheter from the airway. Another step 1520 comprises removing the proximal housing from the first component. Another step 1522 comprises removing the handle of the deflectable catheter from the second component.

Step 1502 can be accomplished using any suitable deflectable catheter system, and skilled artisans will be able to select a suitable deflectable catheter according to a particular embodiment based on various considerations, including the procedure intended to be performed. Example deflectable catheters systems considered suitable to perform method 1500 include deflectable catheter system 602, and any other deflectable catheter system considered suitable for a particular embodiment. An example deflectable catheter system that can be used to accomplish the methods, steps, optional steps, and/or alternative steps described herein is deflectable catheter system 602 and is illustrated and described with respect to FIGS. 18, 19, and 20.

Furthermore, while method 1500 has been described as introducing a deflectable catheter of a deflectable catheter system into an airway, it is considered suitable to deploy a deflectable catheter of a deflectable catheter system into any suitable bodily passage. Skilled artisans will be able to select a suitable bodily passage to deploy a deflectable catheter according to a particular embodiment based on various considerations, including the procedure intended to be performed. Example bodily passages considered suitable include, but are not limited to, sinus passages, airways, sinus cavities, and any other bodily passage considered suitable for a particular application.

Step 1502 can be accomplished by attaching a first attachment member (e.g., the first set of straps) to a first component. The first component can comprise any suitable structure that is positioned at a first location and is capable of receiving a portion of a first attachment member such that the proximal housing can be releasably attached to the first component. Example structures considered suitable to releasably attach a proximal housing include a patient, a patient's arm, a patient's leg, a patient's bed, a medical cart, and any other structure considered suitable for a particular embodiment.

Step 1504 can be accomplished by attaching a second attachment member (e.g., second set of straps) to a second component. The second component can comprise any suitable structure that is positioned at a second location that is different than the first location and that is capable of receiving a portion of a second attachment member such that the handle of the deflectable catheter can be releasably attached to the second component. Example structures considered suitable to releasably attach the handle of a deflectable catheter include a patient, a patient's arm, a patient's leg, a patient's bed, a medical cart, and any other structure considered suitable for a particular embodiment.

Step 1506 can be accomplished by applying a proximal and/or distally directed force on any suitable portion of a deflectable catheter such that it is introduced into an airway.

Step 1508 can be accomplished by applying a distally directed force on any suitable portion of the deflectable catheter such that it advances into the airway.

Step 1510 can be accomplished by applying a proximally directed force on the actuator such that it moves from the actuator first position to the actuator second position. The application of a proximally directed force on the actuator axially advances the wire member in the proximal direction such that the elongate member moves from a straight, or substantially straight, configuration, to a curved configuration in which elongate member defines one or more curves along its length and within the airway. Alternatively, step 1510 can comprise advancing the actuator from the actuator first position to a position between the actuator first position and the actuator second position. Alternatively, step 1510 can be completed such that the elongate member defines a curve outside of the airway.

Step 1512 can be accomplished using any suitable method of obtaining one or more images of an airway, or bodily passage. For example, an imaging device included on a deflectable catheter can be activated such that one or more images are sent to a control board, or other device via wired data transfer cable or wirelessly, as described herein.

An optional step comprises attaching the deflectable catheter to a second device, such as a computer, network, storage device, computer readable storage medium, or any other suitable device, such as those described herein. Another optional step comprises storing the one or more images obtained by the imaging device relative to an interval of time. Another optional step comprises displaying the one or more images obtained by the imaging device.

Step 1514 can be accomplished by completing steps 1506, 1508, 1510, and/or step 1512 and waiting for an interval of time to pass before completing step 1516, 1518, 1520, and/or step 1522. Any suitable interval of time is considered suitable, and skilled artisans will be able to select a suitable interval of time according to a particular embodiment based on various considerations, including the procedure being performed. Example intervals of time considered suitable include, but are not limited to, allowing one or more seconds to pass, one or more minutes to pass, one or more hours to pass, one or more days to pass, and any other interval of time considered suitable for a particular application.

An optional step comprises adjusting the position of the elongate member distal end within the bodily passage. This can be accomplished by applying a force on the actuator such that it moves between the actuator first position and actuator second position and/or applying a force on the deflectable catheter such that is advanced into or withdrawn from the bodily passage.

Step 1516 can be accomplished by applying a distally directed force on the actuator such that it moves from the actuator first position to the actuator second position. The application of a distally directed force on the actuator axially advances the wire member in the distal direction such that the elongate member moves from a curved configuration in which elongate member defines one or more curves along its length to a straight, or substantially straight, configuration. Alternatively, step 1516 can comprise advancing the actuator from the actuator second position, or a position between the actuator second position and the actuator first position, to a position between the actuator first position and the actuator second position.

Step 1518 can be accomplished by placing a proximally and/or distally directed force on any suitable portion of a deflectable catheter such that it is withdrawn from the airway.

An optional step comprises confirming placement of the elongate member and/or that the elongate member defines one or more curves along its length. This optional step can be accomplished using any suitable structure or method of visualization, and skilled artisans will be able to select a suitable structure or method to visualize an elongate member according to a particular embodiment based on various considerations, such as the desired bodily passage within which a deflectable catheter is intended to be deployed. Example structures and methods of visualization include, but are not limited, using direct visualization, fluoroscopy, a scope, transcutaneously, taking an x-ray, and any other method considered suitable for a particular application.

Another optional step comprises performing treatment. This optional step can be completed using any suitable device, system, or component. For example, this optional step can be completed by performing a sleep study on a patient. Alternatively, or in combination with performing a sleep study, this optional step can be completed by introducing a fluid into the irrigation tube to flush the airway. Alternatively, or in combination with performing a sleep study, this optional step can be completed by applying suction to the irrigation tube to withdraw material within the airway. Another optional step comprises cleaning the imaging device. This optional step can be completed by introducing a fluid into the irrigation tube until the imaging device is clean.

Step 1520 can be accomplished by removing the first attachment member from the first component until the proximal housing is free of attachment to the first component.

Step 1522 can be accomplished by removing the second attachment member from the second component until the handle of the deflectable catheter is free of attachment to the second component.

While various steps, alternative steps, and optional steps have been described above with respect to visualizing an airway using a deflectable catheter system, these steps, alternative steps, and optional steps can be included in, accomplished concurrently with, and/or accomplished in the alternative to, the method, steps, alternative steps, and/or optional steps described above with respect to method 500.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A deflectable catheter comprising:
   a handle having an actuator moveable between an actuator first position and an actuator second position;
   an elongate member moveable between a substantially straight configuration when the actuator is in the actuator first position and a curved configuration when the actuator is in the actuator second position, the elongate member comprising:
      a shaft attached to the handle and defining a shaft first lumen and a shaft second lumen;
      a flexible member attached to the shaft, the flexible member having a flexible member proximal end, a flexible member distal end, and defining a flexible member passageway and a helical configuration extending from the flexible member proximal end to the flexible member distal end, the flexible member passageway in communication with each of the shaft first lumen and shaft second lumen; and
      a cap partially disposed within the flexible member lumen and attached to the flexible member;

a wire member having a wire member first end attached to the actuator and a wire member second end attached to the cap, the wire member extending from the wire member first end through the shaft first lumen and through the flexible member passageway;

further comprising an irrigation tube attached to the handle and the cap.

2. The deflectable catheter of claim 1, wherein the shaft has a shaft proximal end, a shaft distal end, and a shaft length that extends from the shaft proximal end to the shaft distal end; and
wherein the flexible member has a flexible member length that extends from the flexible member proximal end to the flexible member distal end, the flexible member length being less than the shaft length.

3. The deflectable catheter of claim 1, wherein a portion of the wire member is disposed between the cap and the flexible member.

4. The deflectable catheter of claim 1, wherein said deflectable catheter has a lengthwise axis;
wherein the shaft first lumen has a shaft first lumen distal end; and
wherein each of the shaft first lumen distal end and the wire member second end is disposed on a plane that extends from said lengthwise axis of said deflectable catheter when the elongate member is in the substantially straight configuration.

5. The deflectable catheter of claim 1, wherein the flexible member comprises a compression spring.

6. The deflectable catheter of claim 1, wherein the flexible member comprises a helically cut portion of a material that forms the elongate member.

7. The deflectable catheter of claim 1, wherein the flexible member is relatively more flexible than the shaft.

8. The deflectable catheter of claim 1, wherein the cap defines a cap opening; and
wherein the wire member is attached to the cap within the cap opening.

9. A deflectable catheter comprising:
a handle having an actuator moveable between an actuator first position and an actuator second position;
an elongate member moveable between a substantially straight configuration when the actuator is in the actuator first position and a curved configuration when the actuator is in the actuator second position, the elongate member comprising:
a shaft attached to the handle and defining a shaft first lumen and a shaft second lumen;
a flexible member attached to the shaft, the flexible member having a flexible member proximal end, a flexible member distal end, and defining a flexible member passageway and a helical configuration extending from the flexible member proximal end to the flexible member distal end, the flexible member passageway in communication with each of the shaft first lumen and shaft second lumen; and
a cap partially disposed within the flexible member lumen and attached to the flexible member;
a wire member having a wire member first end attached to the actuator and a wire member second end attached to the cap, the wire member extending from the wire member first end through the shaft first lumen and through the flexible member passageway;
wherein the cap has a cap proximal end, a cap distal end, and a cap body that defines a cap shaft, a cap flange, a cap opening, and a cap passageway, the cap proximal end disposed within the flexible member passageway, the cap shaft extending from the cap proximal end to the cap flange, the cap opening extending through the cap flange, the cap passageway extending through the cap shaft and cap flange.

10. The deflectable catheter of claim 9, wherein the cap shaft has a first outside diameter and the cap flange has a second outside diameter that is greater than the first outside diameter.

11. The deflectable catheter of claim 9, wherein the handle defines a handle passageway; and
wherein the cap body defines a cap second opening that extends through the cap flange;
further comprising an irrigation tube partially disposed within the handle passageway and the cap second opening, the irrigation tube having an irrigation tube first end, an irrigation tube second end, and defining an irrigation tube lumen extending from the irrigation tube first end to the irrigation tube second end.

12. The deflectable catheter of claim 11, wherein the irrigation tube defines an irrigation tube bend between the irrigation tube first end and the irrigation tube second end.

13. The deflectable catheter of claim 9, wherein the handle includes a control board having a light source;
wherein the cap body defines a cap second opening;
further comprising an optical fiber having an optical fiber first end operatively attached to the light source and an optical fiber second end attached to the cap within the cap second opening.

14. A deflectable catheter comprising:
a handle having an actuator moveable between an actuator first position and an actuator second position;
an elongate member moveable between a substantially straight configuration when the actuator is in the actuator first position and a curved configuration when the actuator is in the actuator second position, the elongate member comprising:
a shaft attached to the handle and having a shaft proximal end, a shaft distal end, a shaft length extending from the shaft proximal end to the shaft distal end, and defining a shaft first lumen and a shaft second lumen;
a flexible member attached to the shaft, the flexible member having a flexible member proximal end, a flexible member distal end, a flexible member length extending from the flexible member proximal end to the flexible member distal end, and defining a flexible member passageway and a helical configuration extending from the flexible member proximal end to the flexible member distal end, the flexible member length being less than the shaft length, the flexible member passageway in communication with each of the shaft first lumen and shaft second lumen; and
a cap partially disposed within the flexible member lumen and attached to the flexible member, the cap defining a cap opening;
a wire member having a wire member first end attached to the actuator and a wire member second end attached to the cap within the cap opening, the wire member extending from the wire member first end through the shaft first lumen and through the flexible member passageway, a portion of the wire member disposed between the cap and the flexible member;
wherein the handle defines a handle passageway; and
wherein the cap has a cap proximal end, a cap distal end, and a cap body that defines a cap shaft, a cap flange, a cap second opening, and a cap passageway, the cap proximal end disposed within the flexible member passageway, the cap shaft extending from the cap proximal end to the cap flange, each of the cap opening and the cap second opening extending through the cap flange, the cap passageway extending through the cap shaft and cap flange;

further comprising an irrigation tube partially disposed within the handle passageway and the cap second opening, the irrigation tube having an irrigation tube first end, an irrigation tube second end, and defining an irrigation tube lumen extending from the irrigation tube first end to the irrigation tube second end.

15. A method of visualizing a bodily passage comprising:
introducing a deflectable catheter having a deflectable catheter proximal end and a deflectable catheter distal end into said bodily passage such that the deflectable catheter distal end is disposed in said bodily passage, the deflectable catheter having a lengthwise axis and comprising:
- a handle having an actuator moveable between an actuator first position and an actuator second position;
- an elongate member moveable between a substantially straight configuration when the actuator is in the actuator first position and a curved configuration when the actuator is in the actuator second position, the elongate member comprising:
  - a shaft attached to the handle and defining a shaft first lumen and a shaft second lumen;
  - a flexible member attached to the shaft, the flexible member having a flexible member proximal end, a flexible member distal end, and defining a flexible member passageway and a helical configuration extending from the flexible member proximal end to the flexible member distal end, the flexible member passageway in communication with each of the shaft first lumen and shaft second lumen; and
  - a cap partially disposed within the flexible member lumen and attached to the flexible member;
- a wire member having a wire member first end attached to the actuator and a wire member second end attached to the cap, the wire member extending from the wire member first end through the shaft first lumen and through the flexible member passageway;
advancing the actuator from the actuator first position to the actuator second position such that the elongate member moves to the curved configuration;
allowing an interval of time to pass;
advancing the actuator from the actuator second position to the actuator first position such that the elongate member moves to the substantially straight configuration; and
removing the deflectable catheter from said bodily passage.

16. The method of claim 15, wherein the elongate member defines a curve within said bodily passage in the second curved configuration.

17. The method of claim 15, wherein the elongate member defines a curve outside of said bodily passage in the second curved configuration.

18. The method of claim 15, wherein the deflectable catheter comprises an irrigation tube attached to the handle and the cap;
further comprising the step of introducing a fluid into the irrigation tube to flush said bodily passage.

19. The method of claim 18, wherein the irrigation tube has an irrigation tube first end, and irrigation tube second end, and defines an irrigation tube lumen and an irrigation tube bend, the irrigation tube lumen extending from the irrigation tube first end to the irrigation tube second end, the irrigation tube bend disposed between the irrigation tube first end and the irrigation tube second end.

* * * * *